(12) United States Patent
Hogarth et al.

(10) Patent No.: US 7,332,631 B2
(45) Date of Patent: Feb. 19, 2008

(54) FC RECEPTOR MODULATING COMPOUNDS AND COMPOSITIONS

(75) Inventors: Mark Phillip Hogarth, Williamstown (AU); Geoffrey Allan Pietersz, Greensborough (AU); Gerard Peter Moloney, West Brunswick (AU)

(73) Assignee: Trillium Therapeutics Inc., Toronto (CA)

( * ) Notice: Subject to any disclaimer, the term of this patent is extended or adjusted under 35 U.S.C. 154(b) by 0 days.

(21) Appl. No.: 10/541,045

(22) PCT Filed: Dec. 24, 2003

(86) PCT No.: PCT/AU03/01734

§ 371 (c)(1),
(2), (4) Date: May 31, 2006

(87) PCT Pub. No.: WO2004/058747

PCT Pub. Date: Jul. 15, 2004

(65) Prior Publication Data

US 2006/0264484 A1   Nov. 23, 2006

(30) Foreign Application Priority Data

Dec. 24, 2002 (AU) .............................. 2002953533

(51) Int. Cl.
*C07C 321/28* (2006.01)
(52) U.S. Cl. ........................................................ 568/42
(58) Field of Classification Search ..................... None
See application file for complete search history.

(56) References Cited

FOREIGN PATENT DOCUMENTS

| | | |
|---|---|---|
| BE | 854857 | 11/1997 |
| DE | 3532280 | 3/1987 |
| EP | 0211670 B | 5/1990 |
| EP | 722729 A | 7/1996 |
| EP | 621255 B | 8/1997 |
| EP | 0434394 B | 8/1998 |
| EP | 920862 A | 6/1999 |
| JP | 2003055340 A | 2/2003 |
| JP | 2003252794 A | 10/2003 |
| WO | WO 95/02406 | 1/1995 |
| WO | WO 95/15323 | 6/1995 |
| WO | WO 00/15214 | 3/2000 |
| WO | WO 01/25193 | 4/2001 |
| WO | WO 02/42289 | 5/2002 |

OTHER PUBLICATIONS

Rolland et al. Tetrahedron Letters 2001 vol. 42, pp. 7563-7566.*
Aldrich Catalogue Handbook of Fine Chemicals 1996-1997, Aldrich Chemical Co. Inc., 2/14 Anella Ave., Castle Hill NSW 2 154, Australia, p. 384.
Hogarth, *Current Opinion in Immunology*, 2002, 14(6):798-802.

* cited by examiner

*Primary Examiner*—Johann Richter
*Assistant Examiner*—Valenrod Yevgeny
(74) *Attorney, Agent, or Firm*—Sheridan Ross P.C.

(57) ABSTRACT

The present invention provides compounds capable of binding to an Fc receptor and modulating Fc receptor activity comprising a core lipophilic group in the form of an Aryl ring substituted with a group rich in p-electrons. The invention further provides for a method of treating an autoimmune disease involving Fc receptor activity using such compounds. A method for obtaining a compound which modulates Fc receptor activity is also provided, the method comprising: (a) providing or designing compounds having structural characteristics to fit in the groove of the FcγRIIa structure; and (b) screening the compounds for modulating activity on the Fc receptor.

4 Claims, 7 Drawing Sheets

FC RECEPTOR MODULATING COMPOUNDS AND COMPOSITIONS

FIELD OF THE INVENTION

The invention relates to a novel class of Fc receptor modulating compounds. More particularly the present invention relates to a pharmaceutical composition comprising an Fc receptor modulating compound in combination with a pharmaceutically acceptable carrier.

BACKGROUND OF THE INVENTION

The immune system, once triggered by a foreign organism, responds by generating a series of molecules, including molecules known as antibodies, which facilitate the destruction of the foreign organism. Autoimmune diseases are a group of disorders characterised by the failure of the immune system to distinguish between foreign and healthy tissue within the body. The immune system then generates antibodies to healthy or normal tissue including bones and joints (rheumatoid arthritis), platelets (immune thrombocytopenia purpura and blood vessels/connective tissue (systemic lupus erythematosus).

Although the trigger for autoimmune diseases is not completely understood, treatments have been developed that inhibit or halt the severity of the damage done to healthy tissue.

Antibodies produced by people suffering autoimmune diseases bind to healthy tissue resulting in formation of 'immune complexes'. These immune complexes bind to receptors on the surface of inflammatory white blood cells, called Fc receptors (FcR). When the immune complex binds to the FcR, white blood cells are activated releasing a series of chemicals known as cytokines into the blood system. These chemicals lead to the destruction of tissue and joints and also propagates the immune response so that attack on healthy tissue continues.

Traditional treatments, such as those for rheumatoid arthritis, include the use of cytotoxic agents such as methotrexate. Methotrexate non-specifically kills all dividing cells, eliminating the cells producing the antibodies. The major side effect of methotrexate is that it non-specifically kills cells of the immune system leaving the patient immuno-supressed. More recently, a number of new products have been launched which inhibit the naturally produced chemicals that lead to tissue/joint destruction. The limitation of some of these products is that they target only one of the many inflammatory chemicals released. For example, Enbrel and Remicade inhibit the action of Tumour Necrosis Factor alpha (TNF) whilst Kineret inhibits Interleukin-1.

It would be understood by the person skilled in the art that although the above discussion principally concerns rheumatoid arthritis, the scope of the present invention is not so limited and the scope extends to other autoimmune diseases such as immune thrombocytopenia purpura, systemic lupus erythematosus and Crohn's disease.

The Fc receptor is a useful target for drug development because it is upstream in the inflammatory process and in theory, preventing the triggering of this receptor should block the release of many of the tissue-damaging chemicals.

FcRs consist of a family of highly related receptors that are specific for the Fc portion of immunoglobulin (Ig). Receptors have been defined for each of the immunoglobulin classes and as such are defined by the class of Ig to which they bind (e.g. Fc gamma receptors (FcγR) bind gamma immunoglobulin (IgG), Fc epsilon receptors (FcεR) bind epsilon immunoglobulin (IgE), Fc alpha receptors (FcαR) bind alpha immunoglobulin (IgA)). Among the FcγR receptors, three sub-family members have been defined; FcγRI, which is a high affinity receptor for IgG; FcγRII, which are low affinity receptors for IgG that bind to aggregates of immune complexes; and FcγRIII, which are low affinity receptors that bind to immune complexes. In recent times, further differentiation of these receptors has been achieved, such as, for example the identification of FcγRIIa.

These receptors are highly related structurally but perform different functions. The structure and function of FcγRII is of interest because of its interaction with immune complexes and its association with disease.

FcγR are expressed on most hematopoietic cells, and through the binding of IgG plays a key role in homeostasis of the immune system and host protection against infection. FcγRII essentially binds only to IgG immune complexes and is expressed on a variety of cell types including, for example, monocytes, macrophages, neturophils, eosinophils, platelets and B lymphocytes. FcγRII is involved in various immune and inflammatory responses including antibody-dependent cell mediated cytotoxicity, clearance of immune complexes, release of inflammatory mediators and regulation of antibody production. The binding of IgG to a FcγR can lead to disease indications that involve regulation by FcγR. For example, thrombocytopenia purpura involves platelet damage resulting from FcγR-dependent IgG immune complex activation of platelets or their destruction by FcγR+ phagocytes. In addition, various inflammatory diseases including rheumatoid arthritis, and systemic lupus erythematosus involve IgG immune complexes.

FcγRs exist at the surface of a cell. In essence, they are dimers of two virtually identical structures which meet in such as way that they define a groove. Structures of these dimers are disclosed in International Patent Application No. WO 99/40117. The Fc portion of aggregated antibody binds to this groove, hence compounds designed to interfere with the binding in the groove may inhibit antibody/receptor binding.

Potentially suitable compounds are derived from random screening as well as rational drug design to modulate Fc receptors. Drug design depends at least in part on the structure of the site to which the compounds are intended to bind. U.S. Pat. No. 6,355,683 has postulated the structure of the binding region of FcγRIIa binding region based on X-ray crystallographic analysis. It is believed that the relevant binding site (that is, the groove) has a lip comprising lysine and histidine residues and represents a target for interaction with hydrogen-bonding and/or acidic groups in a suitable modulator. The wall of the groove contains a phenylalanine benzene ring and may be a target for a hydrophobic interaction, particularly π-π interactions. The 'floor' of the groove includes Phe121, Thr152, Leu159 and Ser161 and together with Asn154, Lys117 (backbone carbonyl) and Thr 119. These proteins are believed to be arranged to form a pocket that is capable of strong hydrogen bonding and/or Van der Waals interactions with a modulator or a ligand.

Because FcRs are involved in a variety of biological mechanisms, it is important that the compounds identified as suitable for affecting the binding of immunoglobulins to FcγR do not adversely affect the other biological functions of FcRs. For example, U.S. Pat. No. 6,355,683 discloses certain classes of aromatic, cyclic and amino acid species that modulate binding of immunoglobulins to Fc receptors.

While many hundreds of species have been identified which affect the binding of immunoglobulins to FcR, their binding affinity and suitability for use in drug formulations varies. Accordingly there is an ongoing need for identification of potential new chemical species that can be used in pharmaceutical compositions for modulation of binding of immunoglobulins to Fc receptors.

SUMMARY OF THE INVENTION

It has now been found that a new group or class of compounds have activity as Fc receptor modulating compounds and may be used in pharmaceutical compositions. These compounds typically have a core lipophilic group, substituted with a group rich in π-electrons, preferably having a delocalised π-electron system. The compounds typically include at least one acidic group having a π-electron system.

In a first aspect, the present invention provides a compound capable of binding to a Fc receptor and modulating Fc receptor activity having the general formula I:

I wherein

R1, R2, R3, R4, R5, are each independently selected from H, halogen, $NO_2$, CN, $C_{1-6}$alkyl, $CF_3$, aryl, heteroaryl, cylcoalkyl, cycloheteroalkyl, $OCF_3$, OR18, SR18, $OC_{1-6}$alkyl, $OC_{2-6}$alkylNR18R19, Oaryl, Oheteroaryl, Ocycloalkyl, Ocycloheteroalkyl, $OC_{1-6}$alkylaryl, $OC_{1-6}$ alkylheteroaryl, $OC_{1-6}$alkylcycloalkyl, $OC_{1-6}$cycloheteroalkyl, $CO_2$R18, $C_{1-6}$alkyl$CO_2$R18, CONR18R19, $C_{1-6}$alkylCONR18R19, NR18R19, $C_{1-6}$alkylNR18R19, NR20$C_{1-6}$alkylNR18R19, $C_{1-6}$alkylNR20$C_{1-6}$alkylNR18R19, NR18COR19, $C_{1-6}$alkylNR18COR19, $C_{1-6}$alkylNR20CONR18R19, NR20CONR18R19, $C_{1-6}$alkylNR18$SO_2$R19, NR18$SO_2$R19;

R18, R19 are each independently selected from H, $C_{1-4}$ alkyl, $C_{1-4}$ alkyl cycloheteroalkyl, aryl, heteroaryl, $C_{1-4}$alkyl aryl, $C_{1-4}$ alkyl heteroaryl, or may be joined to form an optionally substituted 3-8 membered ring optionally containing an atom selected from O, S, NR21;

R20, R21 are each independently selected from H, $C_{1-4}$alkyl;

R6 is selected from H, $C_{1-4}$alkyl;

R7 is selected from H, $C_{1-4}$alkyl, SH, CN;

R8 is selected from OR9, NR9R10;

R9, R10 are each independently selected from H, $C_{1-4}$alkyl, $C_{1-4}$alkyl$CO_2$H, $C_{1-4}$ alkyl cycloheteroalkyl, aryl, heteroaryl, $C_{1-4}$alkyl aryl, $C_{1-4}$ alkyl heteroaryl, or may be joined to form an optionally substituted 3-8 membered ring optionally containing an atom selected from O, S, NR11;

R11 is selected from H, $C_{1-4}$alkyl.

In a second aspect, the present invention provides a compound capable of binding to a Fc receptor and modulating Fc receptor activity having the general formula II:

II wherein

R1, R2, R3, R4, R5, R6, R7, R8, R9, and R10 are each independently selected from H, halogen, $NO_2$, CN, $C_{1-6}$alkyl, $CF_3$, aryl, heteroaryl, cylcoalkyl, cycloheteroalkyl, $OCF_3$, OR18, SR18, $OC_{1-6}$alkyl, $OC_{2-6}$alkylNR18R19, Oaryl, Oheteroaryl, Ocycloalkyl, Ocycloheteroalkyl, $OC_{1-6}$alkylaryl, $OC_{1-6}$alkylheteroaryl, $OC_{1-6}$alkylcycloalkyl, $OC_{1-6}$cycloheteroalkyl, $CO_2$R18, $C_{1-6}$alkyl$CO_2$R18, CONR18R19, $C_{1-6}$alkylCONR18R19, NR18R19, $C_{1-6}$alkylNR18R19, NR20$C_{1-6}$alkylNR18R19, $C_{1-6}$alkylNR20$C_{1-6}$alkylNR18R19, NR18COR19, $C_{1-6}$alkylNR18COR19, $C_{1-6}$alkylNR20CONR18R19, NR20CONR18R19, $C_{1-6}$alkylNR18$SO_2$R19, NR18$SO_2$R19;

R18, R19 are each independently selected from H, $C_{1-4}$ alkyl, $C_{1-4}$ alkyl cycloheteroalkyl, aryl, heteroaryl, $C_{1-4}$alkyl aryl, $C_{1-4}$ alkyl heteroaryl, or may be joined to form an optionally substituted 3-8 membered ring optionally containing an atom selected from O, S, NR21;

R20, R21 are each independently selected from H, $C_{1-4}$alkyl;

R11, R12 are each independently selected from H, $C_{1-4}$alkyl, halogen, $OC_{1-4}$alkyl.

In a third aspect the present invention provides a compound capable of binding to a Fc receptor and modulating Fc receptor activity having the general formula III:

III wherein

R1, R2, R3, R4, R5 and R6 are each independently selected from H, halogen, $NO_2$, CN, $C_{1-6}$alkyl, $CF_3$, aryl, heteroaryl, cylcoalkyl, cycloheteroalkyl, $OCF_3$, OR18, SR18, $OC_{1-6}$alkyl, $OC_{2-6}$alkylNR18R19, Oaryl, Oheteroaryl, Ocycloalkyl, Ocycloheteroalkyl, $OC_{1-6}$ alkylaryl, $OC_{1-6}$alkylheteroaryl, $OC_{1-6}$alkylcycloalkyl, $OC_{1-6}$cycloheteroalkyl, $CO_2$R18, $C_{1-6}$alkyl$CO_2$R18, CONR18R19, $C_{1-6}$alkylCONR18R19, NR18R19, $C_{1-6}$alkylNR18R19, NR20$C_{1-6}$alkylNR18R19, $C_{1-6a}$lkylNR20$C_{1-6}$alkylNR18R19, NR18COR19, $C_{1-6}$alkylNR18COR19, $C_{1-6}$alkylNR20CONR18R19, NR20CONR18R19, $C_{1-6}$alkylNR18SO$_2$R19, NR18SO$_2$R19;

R18, R19 are each independently selected from H, $C_{1-4}$ alkyl, $C_{1-4}$ alkyl cycloheteroalkyl, aryl, heteroaryl, $C_{1-4}$alkyl aryl, $C_{1-4}$ alkyl heteroaryl, or may be joined to form an optionally substituted 3-8 membered ring optionally containing an atom selected from O, S, NR21;

R20, R21 are each independently selected from H, $C_{1-4}$alkyl;

R7 is selected from H, $C_{1-6}$alkyl, CF$_3$, aryl, heteroaryl, cylcoalkyl, cycloheteroalkyl, CO$_2$R18, $C_{1-4}$alkylCO$_2$R18, CONR18R19, $C_{1-4}$alkylCONR18R19, NR18R19, $C_{1-6}$alkylNR18R19, NR20$C_{1-4}$alkylNR18R19, $C_{1-6}$alkylNR20$C_{1-4}$alkylNR18R19, NR18COR19, $C_{1-6}$alkylNR18COR19, $C_{1-6}$alkylNR20CONR18R19, NR20CONR18R19, $C_{1-6}$alkylNR18SO$_2$R19, NR18SO$_2$R19.

In a fourth aspect the present invention provides a compound capable of binding to a Fc receptor and modulating Fc receptor activity having the general formula IV:

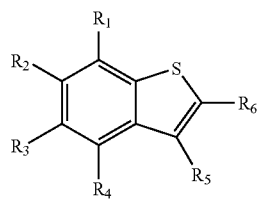

IV wherein

R1, R2, R3, R4, R5 and R6 are each independently selected from H, halogen, NO$_2$, CN, $C_{1-6}$alkyl, CF$_3$, aryl, heteroaryl, cylcoalkyl, cycloheteroalkyl, OCF$_3$, OR18, SR18, OC$_{1-6}$alkyl, OC$_{2-6}$alkylNR18R19, Oaryl, Oheteroaryl, Ocycloalkyl, Ocycloheteroalkyl, OC$_{1-6}$ alkylaryl, OC$_{1-6}$alkylheteroaryl, OC$_{1-6}$alkylcycloalkyl, OC$_{1-6}$cycloheteroalkyl, CO$_2$R18, $C_{1-6}$alkylCO$_2$R18, CONR18R19, $C_{1-6}$alkylCONR18R19, NR18R19, $C_{1-6}$alkylNR18R19, NR20$C_{1-6}$alkylNR18R19, $C_{1-6}$alkylNR20$C_{1-6}$-alkylNR18R19, NR18COR19, $C_{1-6}$alkylNR18COR19, $C_{1-6}$alkylNR20CONR18R19, NR20CONR18R19, $C_{1-6}$alkylNR18SO$_2$R19, NR18SO$_2$R19;

R18, R19 are each independently selected from H, $C_{1-4}$ alkyl, $C_{1-4}$ alkyl cycloheteroalkyl, aryl, heteroaryl, $C_{1-4}$alkyl aryl, $C_{1-4}$ alkyl heteroaryl, or may be joined to form an optionally substituted 3-8 membered ring optionally containing an atom selected from O, S, NR21;

R20, R21 are each independently selected from H, $C_{1-4}$alkyl.

In a fifth aspect, the present invention provides a compound capable of binding to a Fc receptor and modulating Fc receptor activity comprising a core lipophilic group in the form of an Aryl ring substituted with a group rich in π-electrons.

In a sixth aspect, the present invention provides a pharmaceutical composition suitable for modulating Fc receptor activity in an animal comprising one or more compounds according to the first to fifth aspects of the present invention together with a pharmaceutically acceptable diluent.

In a seventh aspect, the present invention provides a method for treating an autoimmune disease involving Fc receptor activity comprising administering to a subject in need of treatment with a pharmaceutical composition according to the sixth aspect of the present invention.

In an eighth aspect, the present invention provides a method for obtaining a compound which modulates Fc receptor activity, the method comprising:

(a) providing or designing compounds having structural characteristics to fit in the groove of the FcγRIIa structure; and (b) screening the compounds for modulating activity on the Fc receptor.

In a ninth aspect, the present invention provides a compound which modulates Fc receptor activity obtained by the method according to the eighth aspect of the present invention.

In a tenth aspect, the present invention provides a method for treating an autoimmune disease involving Fc receptor activity comprising administering to a subject in need of treatment with a pharmaceutical composition containing a compound which modulates Fc receptor activity according to the ninth aspect of the present invention.

In an eleventh aspect, the present invention provides use of composition according to the sixth aspect of the present invention in treatment or therapies for autoimmune diseases involving Fc receptor activity.

In a twelfth aspect, the present invention provides use of a compound according to the first to fifth aspects in the manufacture of a medicament for the treatment of an autoimmune disease.

DETAILED DESCRIPTION OF THE INVENTION

It has now been found that a new group or class of compounds have activity as Fc receptor modulating compounds and may be used in pharmaceutical compositions. These compounds typically have a core lipophilic group, substituted with a group rich in π-electrons, preferably having a delocalised π-electron system. The compounds typically include at least one acidic group having a π-electron system.

In a first aspect, the present invention provides a compound capable of binding to a Fc receptor and modulating Fc receptor activity having the general formula I:

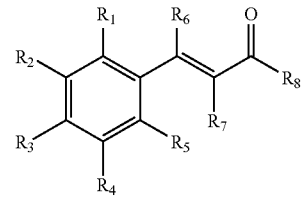

I

R1, R2, R3, R4, R5, are each independently selected from H, halogen, NO$_2$, CN, $C_{1-6}$alkyl, CF$_3$, aryl, heteroaryl, cylcoalkyl, cycloheteroalkyl, OCF$_3$, OR18, SR18, OC$_{1-6}$ alkyl, OC$_{2-6}$alkylNR18R19, Oaryl, Oheteroaryl, Ocycloalkyl, Ocycloheteroalkyl, OC$_{1-6}$alkylaryl, OC$_{1-6}$alkylheteroaryl, OC$_{1-6}$alkylcycloalkyl, OC$_{1-6}$cycloheteroalkyl, CO$_2$R18, $C_{1-6}$alkylCO$_2$R18, CONR18R19, $C_{1-6}$alkylCONR18R19, NR18R19, $C_{1-6}$alkylNR18R19, NR20$C_{1-6}$alkylNR18R19, $C_{1-6}$alkylNR20$C_{1-}$ $_6$alkylNR18R19, NR18COR19, $C_{1-6}$alkylNR18COR19, $C_{1-6}$alkylNR20CONR18R19, NR20CONR18R19, $C_{1-6}$alkylNR18SO$_2$R19, NR18SO$_2$R19;

R18, R19 are each independently selected from H, $C_{1-4}$ alkyl, $C_{1-4}$ alkyl cycloheteroalkyl, aryl, heteroaryl, $C_{1-4}$alkyl aryl, $C_{1-4}$ alkyl heteroaryl, or may be joined to form an optionally substituted 3-8 membered ring optionally containing an atom selected from O, S, NR21;

R20, R21 are each independently selected from H, $C_{1-4}$alkyl;

R6 is selected from H, $C_{1-4}$alkyl,

R7 is selected from H, $C_{1-4}$alkyl, SH, CN;

R8 is selected from OR9, NR9R10

R9, R10 are each independently selected from H, $C_{1-4}$alkyl, $C_{1-4}$alkylCO$_2$H, $C_{1-4}$ alkyl cycloheteroalkyl, aryl, heteroaryl, $C_{1-4}$alkyl aryl, $C_{1-4}$ alkyl heteroaryl, or may be joined to form an optionally substituted 3-8 membered ring optionally containing an atom selected from O, S, NR11

R11 is selected from H, $C_{1-4}$alkyl.

In a preferred embodiment

R1, R2, R3, R4 and R5 are each independently selected from H, OH, OC$_{1-4}$alkyl, OC$_{1-4}$alkylaryl, $C_{1-4}$alkyl, halogen;

R6 is selected from H, $C_{1-4}$alkyl,

R7 is selected from H, $C_{1-4}$alkyl, SH, CN;

R8 is selected from OH, NR9R10;

R9, R10 are each independently selected from H, $C_{1-4}$alkyl, $C_{1-4}$alkylCO$_2$H.

In a second aspect, the present invention provides a compound capable of binding to a Fc receptor and modulating Fc receptor activity having the general formula II:

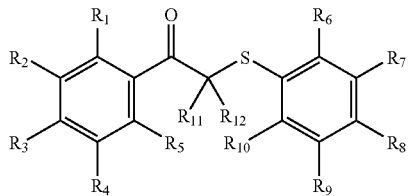

II wherein

R1, R2, R3, R4, R5, R6, R7, R8, R9, and R10 are each independently selected from H, halogen, NO$_2$, CN, $C_{1-6}$alkyl, CF$_3$, aryl, heteroaryl, cylcoalkyl, cycloheteroalkyl, OCF$_3$, OR18, SR18, OC$_{1-6}$alkyl, OC$_{2-6}$alkylNR18R19, Oaryl, Ohetaryl, Ocycloalkyl, Ocycloheteroalkyl, OC$_{1-6}$alkylaryl, OC$_{1-6}$alkylheteroaryl, OC$_{1-6}$alkylcycloalkyl, OC$_{1-6}$cycloheteroalkyl, CO$_2$R18, $C_{1-6}$alkylCO$_2$R18, CONR18R19, $C_{1-6}$alkylCONR18R19, NR18R19, $C_{1-6}$alkylNR18R19, NR20C$_{1-6}$alkylNR18R19, $C_{1-6}$alkylNR20C$_{1-6}$alkylNR18R19, NR18COR19, $C_{1-6}$alkylNR18COR19, $C_{1-6}$alkylNR20CONR18R19, NR20CONR18R19, $C_{1-6}$alkylNR18SO$_2$R19, NR18SO$_2$R19;

R18, R19 are each independently selected from H, $C_{1-4}$ alkyl, $C_{1-4}$ alkyl cycloheteroalkyl, aryl, heteroaryl, $C_{1-4}$alkyl aryl, $C_{1-4}$ alkyl heteroaryl, or may be joined to form an optionally substituted 3-8 membered ring optionally containing an atom selected from O, S, NR21;

R20, R21 are each independently selected from H, $C_{1-4}$alkyl;

R11, R12 are each independently selected from H, $C_{1-4}$alkyl, halogen, OC$_{1-4}$alkyl.

In a preferred embodiment,

R1, R2, R3, R4, R5, R6, R7, R8, R10 are each independently selected from H, $C_{1-4}$alkyl, OC$_{1-4}$alkyl, CO$_2$H, CN;

R11, R12 are each independently selected from H, $C_{1-4}$alkyl.

In a third aspect the present invention provides a compound capable of binding to a Fc receptor and modulating Fc receptor activity having the general formula III:

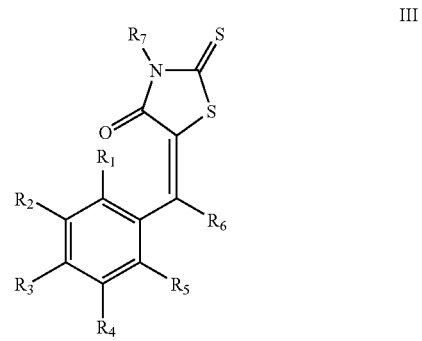

III wherein

R1, R2, R3, R4, R5 and R6 are each independently selected from H, halogen, NO$_2$, CN, $C_{1-6}$alkyl, CF$_3$, aryl, heteroaryl, cylcoalkyl, cycloheteroalkyl, OCF$_3$, OR18, SR18, OC$_{1-6}$alkyl, OC$_{2-6}$alkylNR18R19, Oaryl, Ohetroaryl, Ocycloalkyl, Ocycloheteroalkyl, OC$_{1-6}$alkylaryl, OC$_{1-6}$alkylheteroaryl, OC$_{1-6}$alkylcycloalkyl, OC$_{1-6}$cycloheteroalkyl, CO$_2$R18, $C_{1-6}$alkylCO$_2$R18, CONR18R19, $C_{1-6}$alkylCONR18R19, NR18R19, $C_{1-6}$alkylNR18R19, NR20C$_{1-6}$alkylNR18R19, $C_{1-6}$alkylNR20C$_{1-6}$alkylNR18R19, NR18COR19, $C_{1-6}$alkylNR18COR19, $C_{1-6}$alkylNR20CONR18R19, NR20CONR18R19, $C_{1-6}$alkylNR18SO$_2$R19, NR18SO$_2$R19;

R18, R19 are each independently selected from H, $C_{1-4}$alkyl, $C_{1-4}$alkyl cycloheteroalkyl, aryl, heteroaryl, $C_{1-4}$alkyl aryl, $C_{1-4}$ alkyl heteroaryl, or may be joined to form an optionally substituted 3-8 membered ring optionally containing an atom selected from O, S, NR21;

R20, R21 are each independently selected from H, $C_{1-4}$alkyl;

R7 is selected from H, $C_{1-6}$alkyl, CF$_3$, aryl, heteroaryl, cylcoalkyl, cycloheteroalkyl, CO$_2$R18, $C_{1-4}$alkylCO$_2$R18, CONR18R19, $C_{1-4}$alkylCONR18R19, NR18R19, $C_{1-6}$alkylNR18R19, NR20C$_{1-4}$alkylNR18R19, $C_{1-6}$alkylNR20C$_{1-4}$alkylNR18R19, NR18COR19, $C_{1-6}$alkylNR18COR19, $C_{1-6}$alkylNR20CONR18R19, NR20CONR18R19, $C_{1-6}$alkylNR18SO$_2$R19, NR18SO$_2$R19 wherein R18, R19 are as defined above.

In a preferred embodiment

R1, R2, R3, R4, R5, and R6 are each independently selected from H, halogen, OH, OC$_{1-4}$alkyl, $C_{1-4}$alkyl;

R7 is selected from H, $C_{1-4}$alkyl, $C_{1-4}$alkylCO$_2$H.

In a fourth aspect the present invention provides a compound capable of binding to a Fc receptor and modulating Fc receptor activity having the general formula IV:

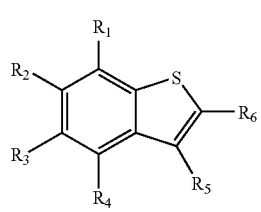

IV

R1, R2, R3, R4, R5 and R6 are each independently selected from H, halogen, $NO_2$, CN, $C_{1-6}$alkyl, $CF_3$, aryl, heteroaryl, cylcoalkyl, cycloheteroalkyl, $OCF_3$, OR18, SR18, $OC_{1-6}$alkyl, $OC_{2-6}$alkylNR18R19, Oaryl, Oheteroaryl, Ocycloalkyl, Ocycloheteroalkyl, $OC_{1-6}$alkylaryl, $OC_{1-6}$alkylheteroaryl, $OC_{1-6}$alkylcycloalkyl, $OC_{1-6}$cycloheteroalkyl, $CO_2R18$, $C_{1-6}$alkyl$CO_2R18$, CONR18R19, $C_{1-6}$alkylCONR18R19, NR18R19, $C_{1-6}$alkylNR18R19, $NR20C_{1-6}$alkylNR18R19, $C_{1-6}$alkyl$NR20C_{1-6}$alkylNR18R19, NR18COR19, $C_{1-6}$alkylNR18COR19, $C_{1-6}$alkylNR20CONR18R19, NR20CONR18R19, $C_{1-6}$alkylNR18SO$_2$R19, NR18SO$_2$R19;

R18, R19 are each independently selected from H, $C_{1-4}$ alkyl, $C_{1-4}$ alkyl cycloheteroalkyl, aryl, heteroaryl, $C_{1-4}$alkyl aryl, $C_{1-4}$ alkyl heteroaryl, or may be joined to form an optionally substituted 3-8 membered ring optionally containing an atom selected from O, S, NR21;

R20, R21 are each independently selected from H, $C_{1-4}$alkyl.

In a preferred embodiment,

R1, R2, R3, R4 are each independently selected from H, halogen, $NO_2$, $OC_{1-4}$alkyl, $C_{1-4}$alkyl;

R5 is selected from H, Cl, $OC_{1-4}$alkyl, $OC_{1-4}$alkylaryl, $OC_{3-6}$cycloalkyl;

R6 is selected from $CO_2H$, CONR$_7$R$_8$;

R7, R8 are each independently selected from H, 5-tetrazole.

In the above description it will be appreciated that:

$C_{1-4}$ alkyl means an unsubstituted or optionally substituted straight or branched alkyl chain.

Aryl means unsubstituted or optionally substituted phenyl or naphthyl.

Heteroaryl means an unsubstituted or optionally substituted 5- or 6-membered heteroaromatic ring containing one or more heteroatoms selected from O, N, S.

Cycloalkyl means an optionally substituted 3-8 membered saturated ring.

Cycloheteroalkyl means an optionally substituted 3-8 membered saturated ring containing 1-3 heteroatoms selected from O, S, NR24, where R24 is H, $C_{1-4}$ alkyl, aryl, heteroaryl.

In a fifth aspect, the present invention provides a compound capable of binding to a Fc receptor and modulating Fc receptor activity comprising a core lipophilic group in the form of an Aryl ring substituted with a group rich in π-electrons.

Preferably, the substituent on the Aryl ring comprises a 5 or 6 membered ring system having π bonds and/or a carbon chain comprising, or substituted with heteroatoms having π electrons. Preferably, the substituted Aryl ring is selected from:

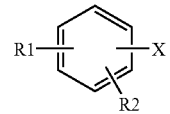

and salts thereof, wherein

R1 is selected from the group —COOH, —COOCH$_3$, —NO$_2$, —OCH$_3$, —OH, —CN, halides and hydrogen, R2 is selected from the group —NO$_2$, —COOH, halides and hydrogen;

X is selected by the group —S(O)Ar(COOH), —S(CH$_2$)$_3$CN, —C(O)CH$_2$SAr(COOH), —C(O)CH$_2$SCH$_2$C(O)Ar(COOH), —NHC(O)NHAr(COOH), —NHC(O)NH[CNC(COOH)NNH], —CH$_2$NCHAr(COOH), —CH$_2$SAr(COOH), —NHCH$_2$Ar(COOH), —NCHAr(COOH), —NCHAr(COOH), —(CH(O)CH)C(O)Ar(COOH), —(CH)$_2$C(O)(C$_4$H$_4$N), —CH$_2$C(SH)COOH,

—CH$_2$OC(O)NH(CH$_2$)$_{2-5}$COOH, —CH$_2$OC(O)NH[CH$_2$C(O)NH]$_2$—CH$_2$COOH,

—CH$_2$OC(O)NH[CH$_2$C(O)NH]$_2$—CH(CH$_3$)COOH, —CH$_2$OC(O)NH(CH$_2$)$_3$COOH,

—CH$_2$NHC(O)NH(CH$_2$)$_{3-5}$COOH, —CH$_2$NHC(O)(CH$_2$)$_{2-3}$COOH,

—CH$_2$CH$_2$O—Ar[(CH)CHC(O)OH], —NHC(O)NH(CH$_2$)$_{3-5}$COOH, —NHNCHAr(COOH) and the ring systems —C(O)Ar(COOH)—, —S(O)C(COOH)C(Cl)—, —SC(COOH)C(Cl)—, —SC(COOH)C(OC$_6$H$_{11}$)— and —SC[C(O)NH—(CN$_4$H)]C[OCH(CH$_3$)$_2$]—, and —C(O)Ar(COOH)(NO$_2$)—.

The aromatic compound may be, for example, a substituted Aryl ring (Ar) selected from:

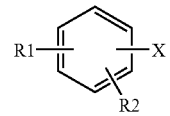

or salts thereof, wherein when X is chosen from the group —S(O)Ar(m-COOH) [032], —S(CH$_2$)$_3$CN [239], —C(O)CH$_2$SAr(m-COOH) [217], —C(O)CH$_2$SCH$_2$C(O)Ar(m-COOH) [292], —NHC(O)NHAr(m-COOH) [192], —NHC(O)NH[CNC(COOH)NNH][219], —CH$_2$NCHAr(m-COOH) [200], —CH$_2$SAr(m-COOH) [255], —NHCH$_2$Ar(m-COOH) [100], —NCHAr(m-COOH) [076], —NCHAr(p-COOH) [081] or —(CH(O)CH)C(O)Ar(m-COOH) [027], R1 is —COOH, located at position 3 on the aryl ring and R2 is hydrogen;

when X comprises a ring system —C(O)Ar(m-COOH)— [001], R1 is —COOH located at position 3 on the aryl ring and R2 is hydrogen;

when X comprises a ring system —S(O)C(COOH)C(Cl)— [044] or —SC(COOH)C(Cl)— [026], R1 is —NO$_2$ located at position 6 on the aryl ring and R2 is hydrogen;

when X comprises a ring system —SC(COOH)C(OC$_6$H$_{11}$)— [276], R1 is —OCH$_3$ located at position 5 on the aryl ring and R2 is hydrogen;

when X comprises a ring system —SC[C(O)NH—(CN$_4$H)]C[OCH(CH$_3$)$_2$]— [090], R1 is —OCH$_3$ located at position 7 on the aryl ring and R2 is hydrogen;

when X is the ring system —C(O)Ar(m-COOH)(m-NO$_2$)— [261], R1 and R2 are —NO$_2$ located at positions 3 and 5 on the aryl ring;

when X is the fused heteroatomic fused ring system —SC[C(O)NH(CN$_4$H)]C[OCH(CH$_3$)$_2$]— [092], R1 is —OCH$_3$ located at position 5 on the aryl ring and R2 is —NO$_2$ located at position 4 on the aryl ring;

when X is —(CH)$_2$C(O)(C$_4$H$_4$N) [238], R1 is —COOH located at position 2 on the aryl ring and R2 is hydrogen;

when X is —C(O)(CH)2Ar [237], R1 is COOH located at position 4 on the aryl ring and R2 is hydrogen;

when X is —CH$_2$C(SH)COOH [297], R1 is —OH located at position 2 on the aryl ring and R2 is hydrogen;

when X is —C(O)CH$_2$S—Ar(m-COOH) [216][294], R1 is —CN or H located at position 3 on the aryl ring and R2 is hydrogen;

when X is chosen from the group comprising —CH$_2$OC(O)NH(CH$_2$)$_{2-5}$COOH, [197, 233, 336, 355], —CH$_2$OC(O)NH[CH$_2$C(O)NH]2-CH$_2$COOH [234], —CH$_2$OC(O)NH[CH$_2$C(O)NH]$_3$CH(CH$_3$)COOH [235], —[CH$_2$OC(O)NH]$_2$CH$_2$COOH [236], —CH$_2$NHC(O)NH(CH$_2$)$_{3-5}$COOH [337 to 339], —CH$_2$NHC(O)(CH$_2$)$_{2-3}$COOH [343, 344], —CH$_2$O—Ar[(p-CH)CHC(O)OH [299] and —CH$_2$NCHAr(m-COOH) [331] both R1 and R2 are hydrogens;

when X is chosen from the group —NHC(O)NH(CH$_2$)3-5COOH [340, 341, 342] then R1 is —COOCH$_3$ located at position 3 on the aryl ring and R2 is hydrogen;

when X is chosen from the group —NCHAr(m-COOH) [114] then R1 and R2 are —COOH located at positions 3 and 5 on the aryl ring; and when X is chosen from the group —NHNCHAr(m-COOH) [080] then R1 and R2 are —Cl located at positions 3 and 5 on the aryl ring.

Where used herein the numbers in square brackets correspond to the compounds listed in Table 1.

The numbering used herein has been kept as close as possible to the IUPAC convention nomenclature. In particular when X is located at a single position on the Aryl ring the numbering of the positions on the aryl ring is as follows:

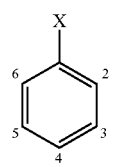

For example, compounds [153], [032], [294], [297], [197], [216], [238], [237], [152], [239], [217], [299], [292] and [113] follow this numbering scheme.

When X is a fused heteroatomic ring system (where Y is nitrogen or sulphur), the numbering on the aryl ring is as follows:

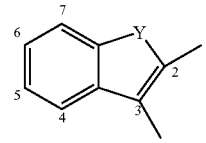

For example, compounds [044], [026], [276], [090] and [092] follow this numbering scheme.

In a preferred embodiment, the compound is selected from compounds [197], [216], [217], [238], [239], [261], [294], [297] and [299]. More preferably the compound is selected from [197] and [294].

In a sixth aspect, the present invention provides a pharmaceutical composition suitable for modulating Fc receptor activity in an animal comprising one or more compounds according to the first to fifth aspects of the present invention together with a pharmaceutically acceptable diluent.

In a seventh aspect, the present invention provides a method for treating an autoimmune disease involving Fc receptor activity comprising administering to a subject in need of treatment with a pharmaceutical composition according to the sixth aspect of the present invention.

In an eighth aspect, the present invention provides a method for obtaining a compound which modulates Fc receptor activity, the method comprising:

(a) providing or designing compounds having structural characteristics to fit in the groove of the FcγRIIa structure; and (b) screening the compounds for modulating activity on the Fc receptor.

In a preferred form, step (a) comprises functionalising the compounds with one or more substituent groups.

Preferably, the compounds are screened by a FcγRIIa dependent platelet activation assay and/or aggregation assay where platelets are activated using heat aggregated human immunoglobulin G as an immune complex. The compounds can be tested in a collagen-arthritis model in FcγRIIa transgenic animals. Such a model is disclosed, for example, in PCT/AU03/00718 entitled "Transgenic Animal Model for Autoimmune Disease" in the name of Arthron Ltd.

If desired the compounds may be screened by measuring the inhibition of an Fc receptor to a ligand in an ELISA based system. For example, if the receptor is Fcγ receptor, the ligand used may be selected from heat aggregated IgG (HAGG) or monomeric IgG or the like.

In a ninth aspect, the present invention provides a compound which modulates Fc receptor activity obtained by the method according to the eighth aspect of the present invention.

In a tenth aspect, the present invention provides a method for treating an autoimmune disease involving Fc receptor activity comprising administering to a subject in need of treatment with a pharmaceutical composition containing a compound which modulates Fc receptor activity according to the ninth aspect of the present invention.

In an eleventh aspect, the present invention provides use of composition according to the sixth aspect of the present invention in treatment or therapies for autoimmune diseases involving Fc receptor activity.

In a twelfth aspect, the present invention provides use of a compound according to the first to fifth aspects in the manufacture of a medicament for the treatment of an autoimmune disease.

Typically, the autoimmune disease involves aggregates of antibodies are produced or where immune complexes are produced by contact of antibody with intrinsic or extrinsic antigen causing damage to normal tissue of an individual.

In a particularly preferred embodiment of the present invention, modulation of Fc receptors by the above identified compounds is used to treat a disease where aggregates of antibodies are produced or where immune complexes are produced by contact of antibody with intrinsic or extrinsic antigen. Modulation of Fc receptors by the above identified compounds can also be used to reduce IgG-mediated tissue damage, to reduce IgE-mediated response and/or to reduce inflammation in a patient.

The present invention provides a variety of compounds which can modulate the interaction between Fc receptors and immunoglobulins. Without wishing to be bound by theory it is believed that these compounds interfere with the groove, or dimerization interface between two FcγRII proteins, thereby affecting cellular signal transduction through one or both of the FcR proteins. Specifically, it is believed that peptide residues 117-131 and 150-164 of FcγRII make up the interfacial area of the FcγRIIa dimer, and the compounds of the present invention may mimic or bind to these regions and thus have activity as good binding modulators.

Specifically, and again without wishing to be bound by theory, it is believed that the compounds of the present invention can provide strong π-π interaction and/or hydrogen-bonding with the wall of the groove while the hydrogen bonding an/or acidic groups interact with the amino acid residues at the lip and floor of the groove.

Compounds of the invention may also bind to other regions of the receptor, as indicated by computer modelling or "docking". For example, some compounds may bind to the FG loop of the Fcγ receptor, or to areas around tryptophan residues such as Trp90 or Trp 113.

It is to be understood that the scope of this invention includes isomers of the relevant compounds and mixtures thereof. Furthermore compounds of the present invention having chiral centres may be synthesised enantioselectively or a mixture of enantiomers and/or diastereomers can be prepared and separated. The resolution of the diasteromers may be carried out by any procedure known in the art. When the compounds of the present invention contain an olefin moiety which can be either of cis- or trans-configuration, the compounds can be synthesized to produce cis- or trans-olefin selectively as the predominant product. Alternatively the compounds containing an olefin moiety can be produced as a mixture of cis- and trans-olefins and separated using known procedures.

The compounds of the present invention may form salts with acids when a basic functional group is present and salts with bases when an acid functional group is present. All such salts are useful in the isolation and/or purification of the new compounds. Of particular value are the pharmaceutically acceptable salts with both acids and bases. Suitable acids include, for example hydrochloric, oxalic, sulphuric, nitric, benzenesulphonic, toluenesulphonic, acetic, maleic, tartaric and the like which are pharmaceutically acceptable. Basic salts for pharmaceutical use include sodium, potassium, calcium and magnesium salts.

Selection

The compounds of the present invention are preferably selected according to the following protocol:

(a) Potentially suitable compounds are designed on the basis of their structural characteristics and likely fit in the groove of the FcγRIIa structure; part of the design process is to modify the compounds by functionalising them with one or more substituent groups;

(b) The compounds identified at (a) are subjected to an in vitro screening program to identify those with the best activity:

(i) Evaluation of Inhibitory Activity in vitro

The compounds of Table 1 were screened in a FcγRIIa dependent platelet activation assay and/or aggregation assay where platelets are activated using heat aggregated human immunoglobulin G as an immune complex. Compounds inhibiting this process were then tested for specificity. Note that the platelets were used as the target as the only Fc receptor expressed on these cells is FcγRIIa. In addition, they are very difficult to inhibit and therefore this assists in identifying compounds with reasonable potency.

The compounds may also be screened using an ELISA inhibition assay to detect the blockade of IgG interaction with FcγRIIa.

(ii) Evaluation of Specificity of Inhibitors in vitro

The compounds were tested for activity against other platelet activation pathways. These were principally induced by arachidonic acid and/or ADP—some of these compounds have also been tested for their capacity to inhibit collagen and/or thrombin induced platelet activation.

(iii) Evaluation of in vitro Potency

The specific inhibitory compounds were then titrated in the platelet activation assay.

(iv) Evaluation of in vivo Potency

Compounds showing best activity were tested in the collagen-arthritis model in FcγRIIa transgenic animals.

Table 2 depicts the compounds that displayed the most promising activities.

Preferably the compounds of the present invention modulate Fc receptors selected from the group consisting of FcαR, FcεR, FcγR, and mixtures thereof, more preferably from the group consisting of FcγRIIa, FcγRIIb, FcγRIIb, FcγRIIc and mixtures thereof and most preferably the FcγRIIa receptor. The compounds of the present invention can be used in a variety of applications including treatment or diagnosis of any disease where aggregates of antibodies are produced and where immune complexes are produced by contact of antibody with intrinsic or extrinsic antigen. Exemplary treatments and diagnosis applicable by the compounds of the present invention include immune complex diseases; autoimmune diseases including but not limited to rheumatoid arthritis, systemic lupus erythematosus, immune thrombocytopenia, neutropenia, hemolytic anaemias; vasculities including but not limited to polyartheritis nodosa, systemic vasculitis; xenograft rejection; and infectious diseases where FcR uptake of virus enhances infection including but not limited to flavivirus infections such as Dengue virus-dengue hemorrhagic fever and measles virus infection. The compounds of the present invention can also be used to reduce IgG mediated tissue damage and to reduce inflammation.

The compounds of the present invention can also enhance leukocyte function by enhancing FcR function. These functions include antibody dependent cell mediated cytotoxicity, phagocytosis, release of inflammatory cytokines. Exemplary treatments and diagnosis for enhanced FcR function include any infection where normal antibodies are produced to remove the pathogen; and any disease requiring FcR function where natural or recombinant antibodies can be used in treatment such as cancer and infections, for example the antibody can be administered in combination with the compound of the present invention to enhance the effect of the antibody treatment.

The compounds of the present invention can be administered to a patient to achieve a desired physiological effect. Preferably the patient is an animal, more preferably a mammal, and most preferably a human. The compound can be administered in a variety of forms adapted to the chosen route of administration, that is, orally or parenterally. Parenteral administration includes administration by the following routes: intravenous; intramuscular; subcutaneous; intraocular; intrasynovial; transepithelially including transdermal, ophthalmic, sublingual and buccal; topically including opthalmic, dermal, ocular, rectal and nasal inhalation via insufflation and aerosol; intraperitoneal; and rectal systemic.

The active compound can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound may be incorporated with excipient and used in the form of ingestible tablets, buccal tablets, troches, capsules, elixers, suspensions, syrups, wafers, and the like.

Such compositions and preparations can contain any therapeutically effective amount of active compound.

The tablets, troches, pills, capsules and the like can also contain the following: a binder such as gum tragacanth, acacia, corn starch or gelatine; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavouring agent such as peppermint, oil of wintergreen, or cherry flavouring. When the dosage unit form is a capsule, it can contain, in addition to materials of the above type, a liquid carrier. Various other materials can be present as coatings or to otherwise modify the physical form of the dosage unit. For instance, tablets, pills or capsules can be coated with shellac, sugar or both. A syrup or elixir can contain the active compound, sucrose as a sweetening agent, methyl and propylparabens as preservatives, a dye and flavouring such as cherry or orange flavour. Of course, any material used in preparing any dosage unit form should be pharmaceutically pur and substantially non-toxic in the amounts employed. In addition, the active compound can be incorporated into sustained-release preparations and formulations.

The active compound can also be administered parenterally. Solutions of the active compound as a free base or pharmacologically acceptable salt can be prepared in water suitably mixed with a surfactant such as hydroxypropylcellulose dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacteria and fungi. The carrier can be a solvent of dispersion medium containing, for example, water, ethanol, polyol (e.g. glycerol, propylene glycol, and liquid polyethylene glycol, and the like), suitable mixtures thereof, and vegetable oils. The proper fluidity can be maintained, for example, by the use of surfactants. The prevention of the action of microorganisms can be brought bout by various antibacterial and antifungal agents, for example, parabens, chlorbutanol, phenol, sorbic acid, thimerosal and the like. In many cases it will be preferable to include isotonic agents such as sugars or sodium chloride. Prolonged absorption of the injectable compositions of agents delaying absorption such as aluminum monostearate and gelatin.

Sterile injectable solutions are prepared by incorporating the active compound in the require amount in the appropriate solvent with various other ingredients as required, followed by filtered sterilisation. Generally, dispersions are prepared by incorporating the various sterilised active ingredients into a sterile vehicle which contains the basic dispersion medium and the required other ingredients. In the case of sterile powders for the preparation of sterile injectable solutions, the preferred drying technique which yield a powder of the active ingredient plus any additional desired ingredient from previously sterile-filtered solution thereof.

The therapeutic compounds of the present invention can be administered to a mammal alone or in combination with pharmaceutically acceptable carriers, as noted above, the proportion of which is determined by the solubility and chemical nature of the compound, chosen route of administration and standard pharmaceutical practice. The compounds may also be co-administered with other agents such as methotrexate, Enbrel, Ramicade, Kinaret or the like.

Additional aspects, advantages, and novel features of this invention will become apparent to those skilled in the art upon examination of the following non-limiting examples and the Figures in which.

Figure 2A:
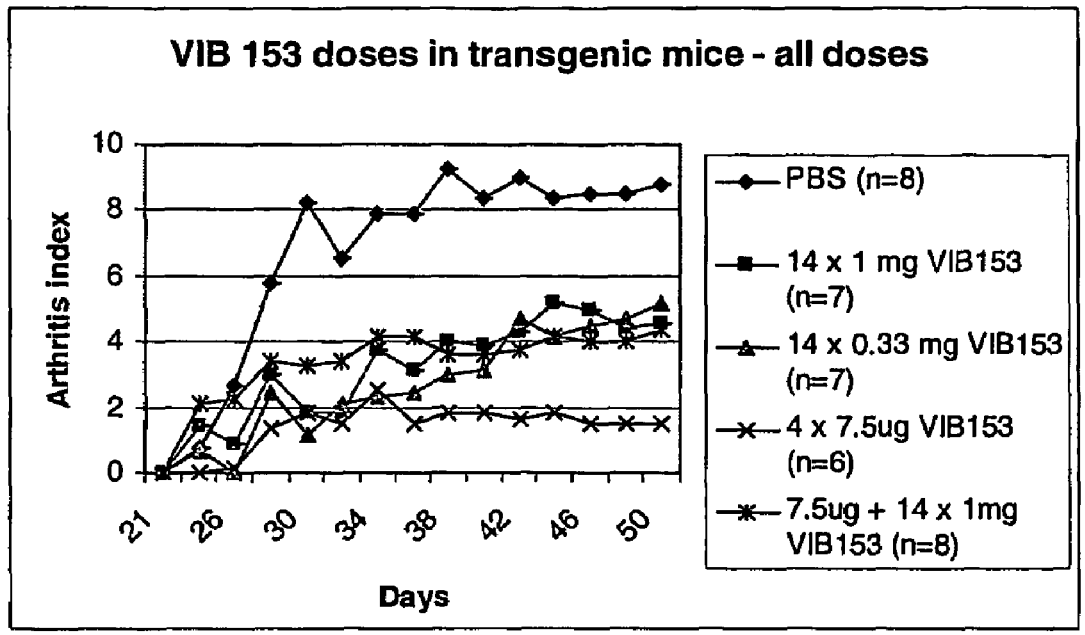
FIG. 2(a) is a graph of Arthritis Index as a function of time (in days) for treatment of FcγRIIa transgenic mice with compound [153] using four different dosage regimes, as compared with phosphate buffered saline (PBS)
Figure 2B:
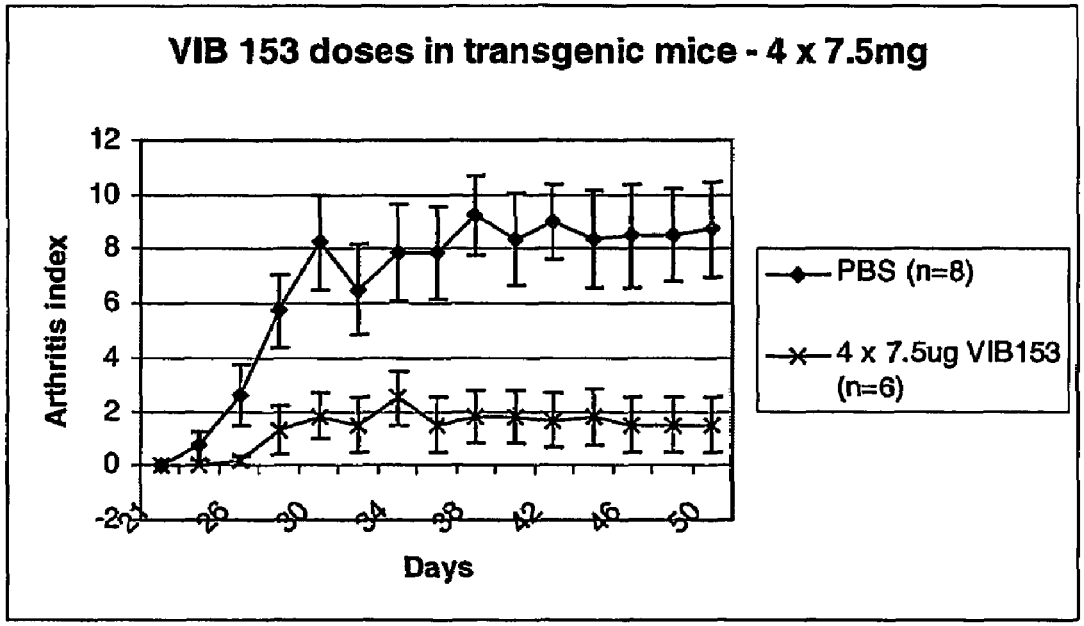
Figure 2C:
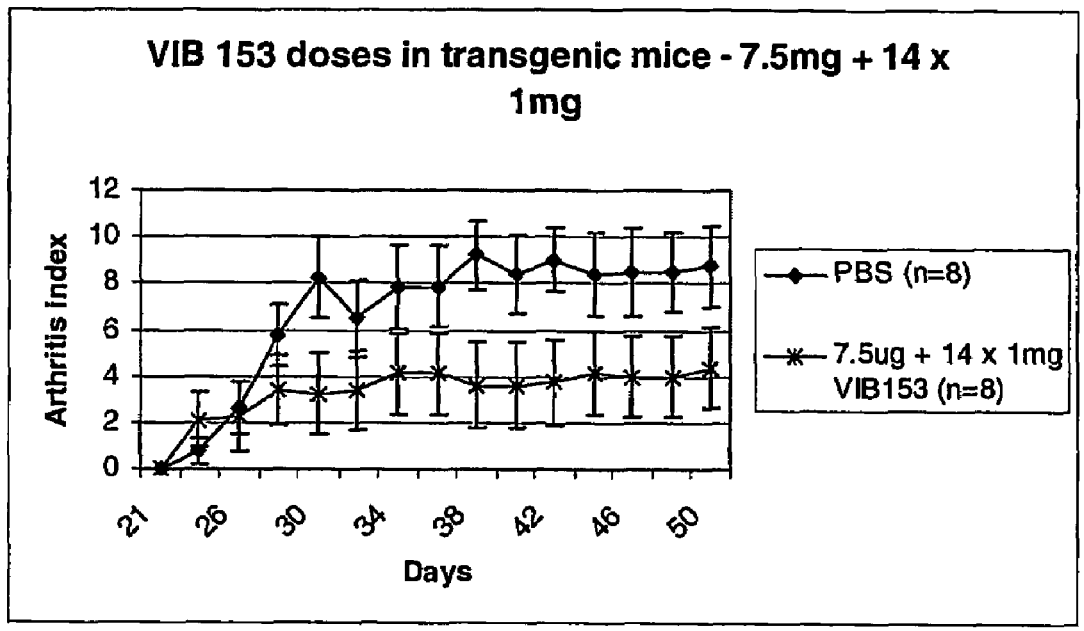
Figure 2C:
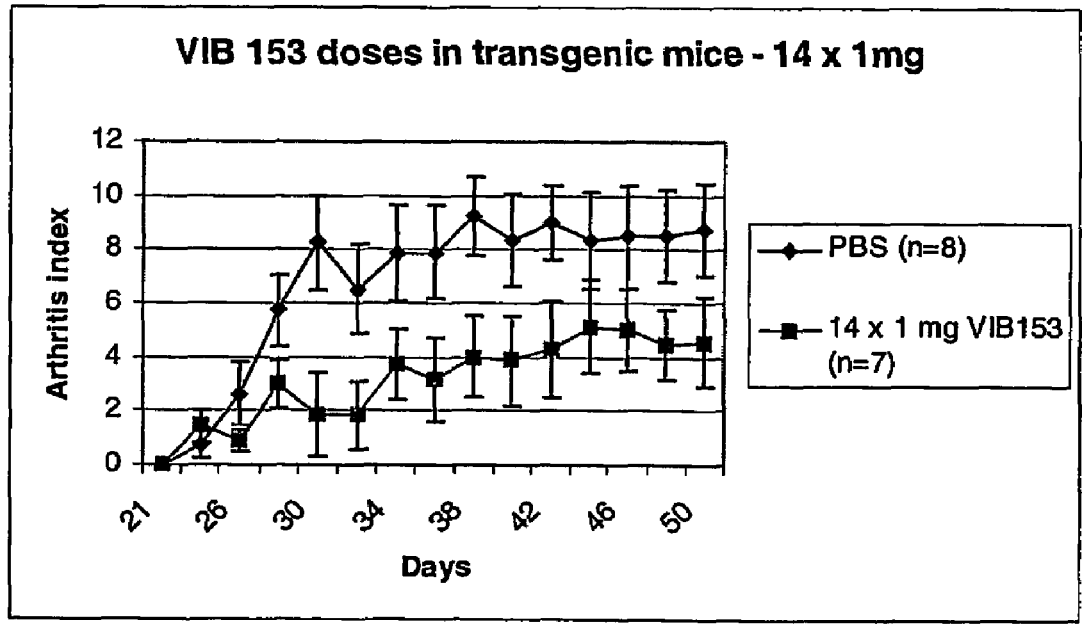
Figure 2D:
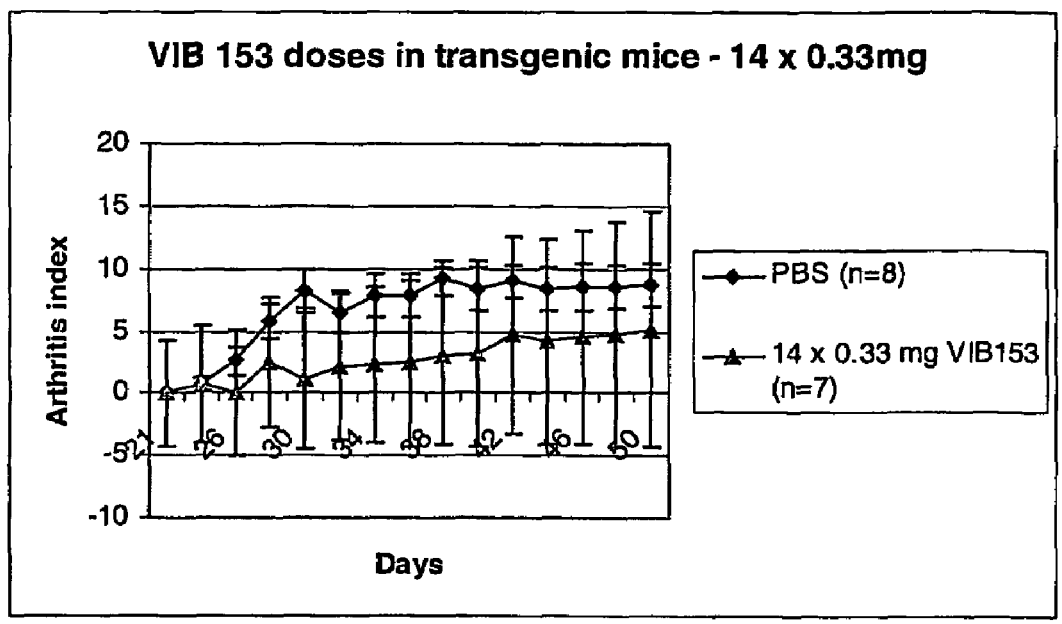
Figure 2E:
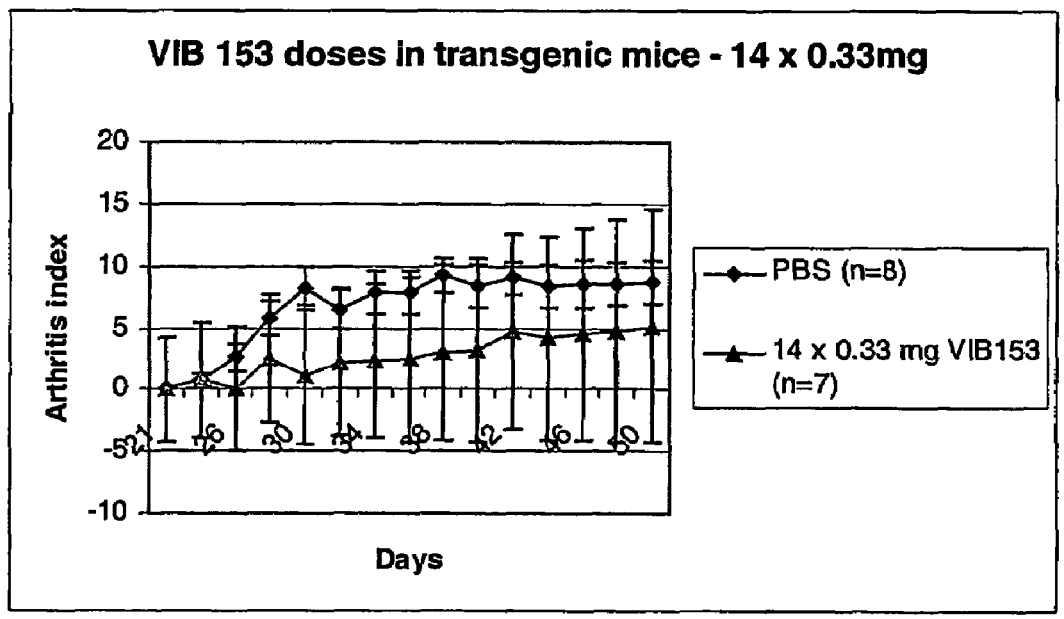
Figure 3:
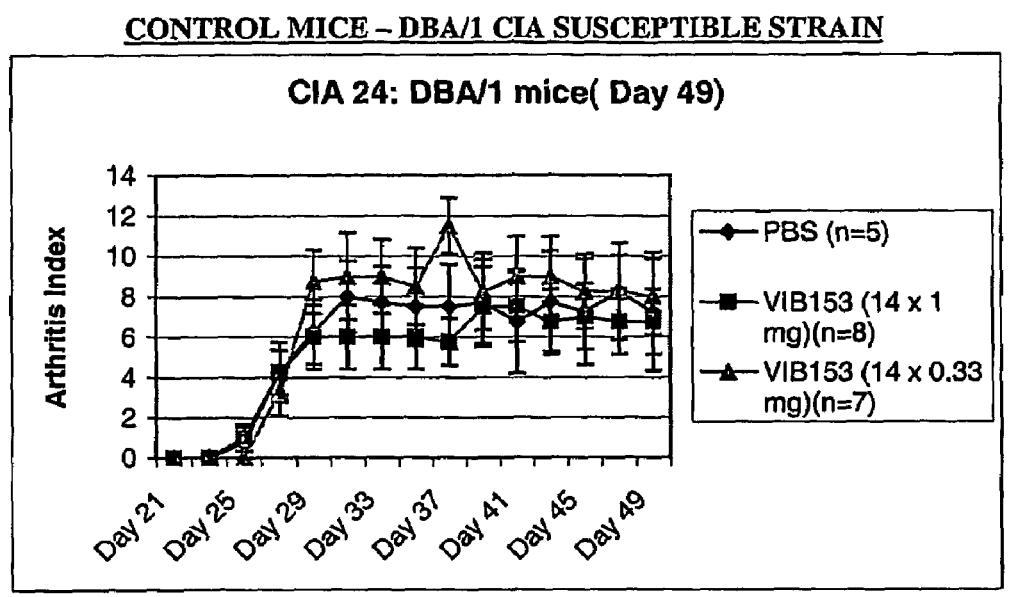
Figure 4:
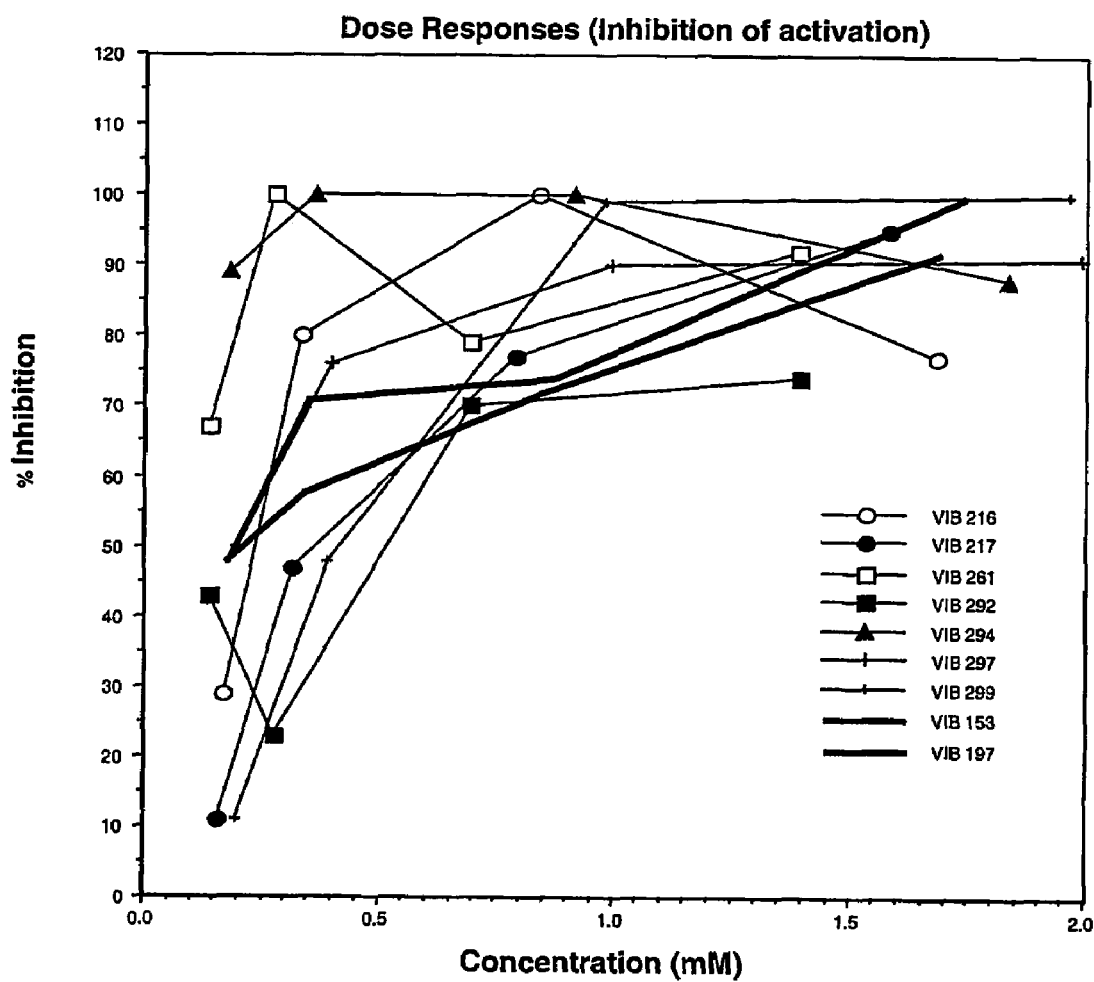
Figure 5:
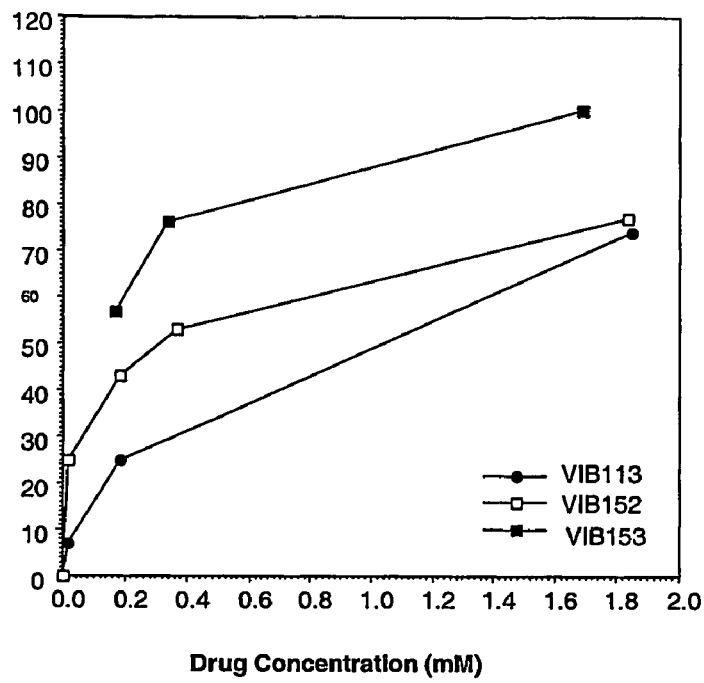
Figure 6:
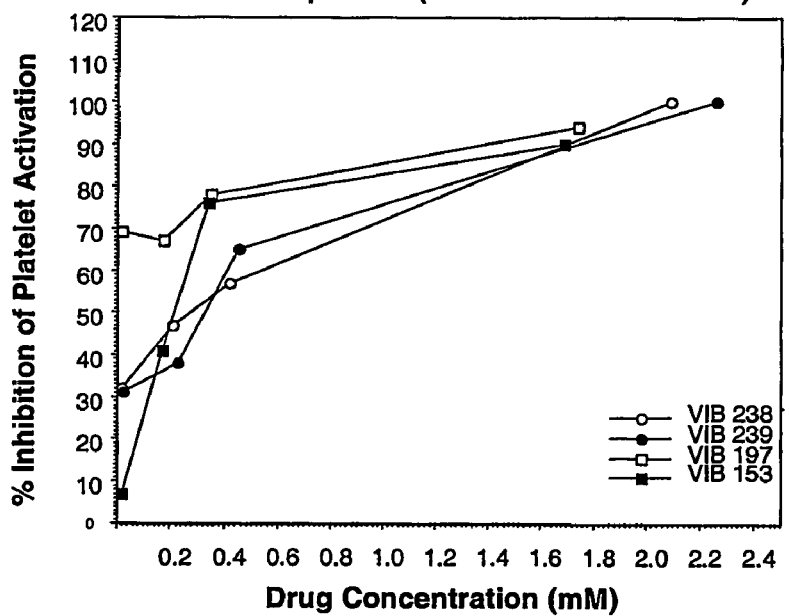

FIGS. 2(b) to (e) which depict the individual dosage regimes of FIG. 2(a) with error bars, as compared with PBS;

FIG. 3 is a graph of Arthritis Index against time in Days for treatment of control mice (non-transgenic mice) with compound [153] as compared with PBS;

FIG. 4 is a graph of % Inhibition of IgG induced platelet activation against compound Concentration (mM) for some of the compounds of the present invention;

FIG. 5 is a graph of % Inhibition of Platelet Activation against compound Concentration (mM) for further compounds of the present invention; and FIG. 6 is a graph of % Inhibition of Platelet Activation against compound Concentration (mM) for compounds VIB 238, 239 and 197 of the present invention.

EXAMPLE

The compounds of the present invention were selected on the basis of their in vitro and in vivo activity as follows;

(i) In vitro Assays

The compounds of the present invention were initially screened in a rapid FACS screening assay, measuring activation of human platelets by heat aggregated IgG. Platelets have only one type of Fcγ receptor, FcγRIIa, hence the use of human platelets eliminated the confounding effects of other Fcγ receptors. In addition, platelets are very sensitive to a range of stimuli and activate rapidly. Activation is measured by the appearance of the protein P-Selectin on the platelet membrane after exposure to various stimuli. The stimuli were heat aggregated with IgG and as specificity controls, collagen or thrombin.

Figure 1A:
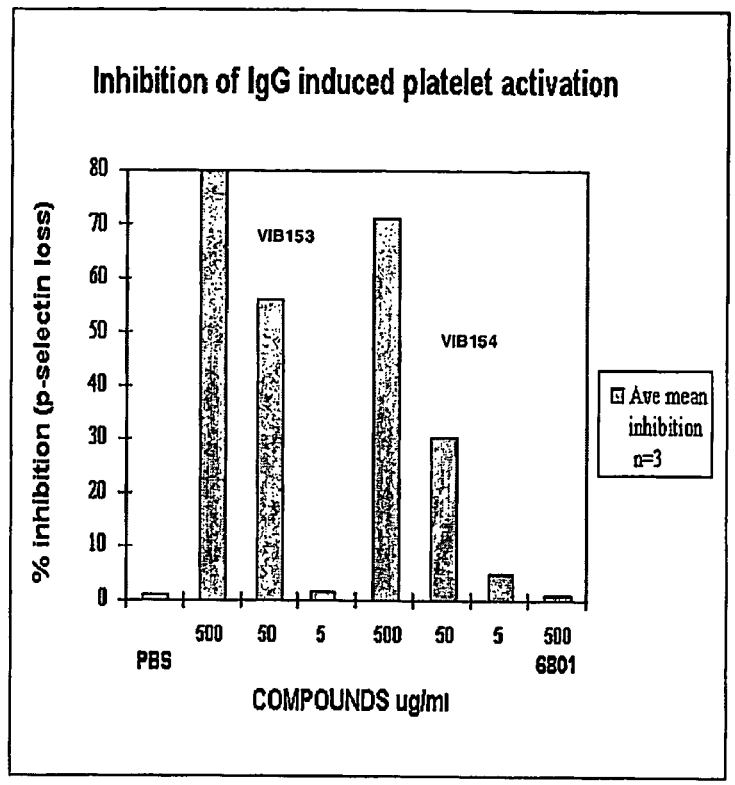
FIG. 1(a) is a graph of % Inhibition (p-selectin loss) against dosage level, illustrating inhibition of IgG induced platelet activation as a function of dose responses using FACS.
Figure 1B:
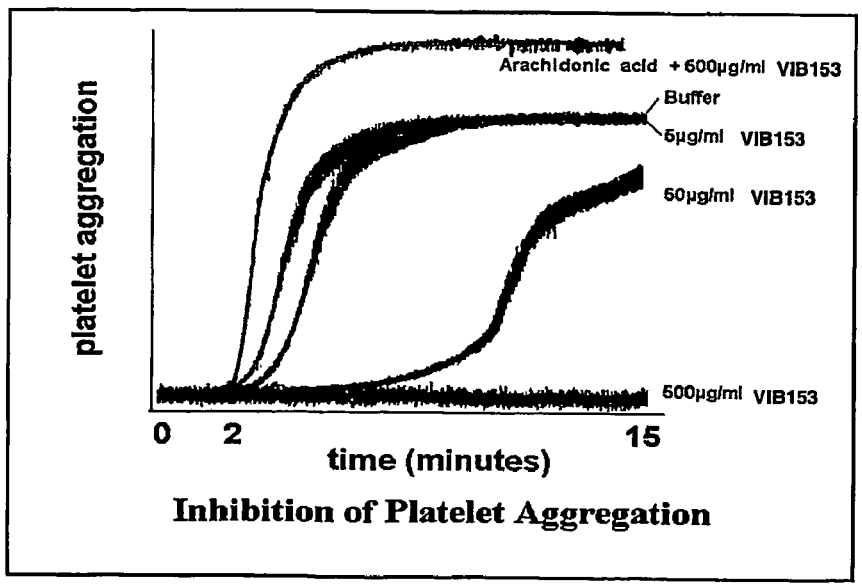
FIG. 1(b) is a graph depicting inhibition of Platelet Aggregation by compound [153] as a function of time (in minutes)

Specifically, this assay utilises washed platelets and heat aggregated IgG (HAGG) as an immune complex (agonist) to activate and crosslink FcγRIIa. Because this is a primary screen a single concentration of small molecule inhibitor is added to the platelets (final concentration of 500 μg/ml) and allowed to incubate for 30 minutes. Heat Aggregated IgG (HAGG) (40 μg/ml) is then added to the platelets and allowed to incubate for 30 minutes. Paraformaldehyde is added to the platelets for 30 minutes prior to washing. Anti-P-Selectin (FITC conjugated) and Anti-CD41 (PE conjugated) are added and the platelets are then screened by FACS to detect expression of P-Selectin, a marker of platelet activation and CD41, which is expressed by all viable platelets. The dose response results generated using FACS for compounds [153] and [154] are depicted in FIG. 1($a$).

Compounds that inhibited platelet activation were then screened using a second, more comprehensive platelet aggregation assay. This assay was used to confirm that the drug compounds cannot only prevent activation but also the aggregation that follows such activation. The aggregation process is extremely difficult to inhibit and is one of the most potent biological cell activation systems known. Compounds that are able to inhibit this process were preferred candidates for in vivo studies (described below).

The specificity of the compounds of the present invention was confirmed by testing for inhibition of other platelet stimuli including thrombin, ADP, arachidonic acid and collagen. The specificity assay compares the effects of the small molecule inhibitors on HAGG (FcγRIIa) activation and the unrelated activation by arachidonic acid, ADP and/or thrombin which are potent stimulators of platelets. This assay also indicates that the small molecule inhibitor has not killed the platelets.

400 μl of washed platelets are incubated in the presence of a range of concentrations of small molecule inhibitor. The agonist, eg HAGG (200 μg/ml) is then added and aggregation measured in an aggregometer, as described by others (Ozaki, Y.; 1998, Sysmex Journal International 8:15; Gratacap M. P. et al; Blood 96:3439 and Gross B. S. et al (1999) Blood 94:4166).

The compounds selected to proceed to in vitro testing had to have specificity for FcγRIIa based on these assays and those that inhibit other mechanisms of platelet activation did not proceed to in vitro testing. The performance of compound [153] in this assay is depicted in FIG. 1($b$) which shows the functionality of the platelets in response to stimulus by arachidonic acid after drug treatment.

In summary, for each compound tested the activity was measured as a function of inhibition of platelet activation and/or platelet aggregation as detailed above. Specificity is defined as specific inhibition of immune complex induced platelet activation but with no effect on arachidonic acid induced activation (and where tested no effect on thrombin, collagen or ADP induced activation).

Compounds were also screened using an ELISA Inhibition Assay. Human Serum Albumin genetically fused to FcγRIIa (HSA-FcγRIIa) was bound to an ELISA plate at a concentration of 5 μg/ml. The small molecule inhibitors were titrated from a starting concentration of 5 mg/ml and allowed to incubate in the presence of the receptor. A human IgG complex (0.2 μg/ml) is then added to the plate and the extent of inhibition of IgG binding by the small molecule inhibitors was measured using HRP labelled anti-human antibody.

Other cell based assays may also be used in addition to the above. For example, assays that measure events dependent on Fc receptor modulation such as $Ca^{2+}$ mobilisation or cytokine production may be used.

(ii) In vivo Testing

Genetically engineered mice were used to test the interaction of the compounds of the present invention with the human form of the FcγRIIa prior to clinical studies. The mice used have the human form of FcγRIIa genetically inserted into their DNA so that the mice produce human receptors on the surface of their inflammatory white blood cells and platelets. Specifically the mice used were C57BL/6/SJL, H-2b inbred mice expressing the FcγRIIa transgene on platelets, neutrophils and macrophages at physiological levels. The severity of arthritis in mice was considerably greater in the FcγRIIa transgenic mice than in normal control mice that do not express the receptor.

Collagen-induced arthritis was chosen as a suitable model for testing the in vivo activity of a selection of compounds of the present invention. Mice were immunised with collagen, and boosted 21 days later at which time they were given the first dose of one of the compounds. The induction of arthritis using collagen was carried out according to the well described methods (Campbell, Bendele et al, 1997, *Ann. Rheum. Dis.* 56(6): 364-8). An emulsion is formed by combining 2 mg/ml chicken collagen type II dissolved in 10 mM acetic acid in an equal volume of Complete Freund's Adjuvant. One hundred microlitres of the emulsion was injected intradermally at the base of the tail. The same dose was prepared and administered proximal to the primary site 21 days later.

Four dosing regimes were tested, each commencing 21 days after the abovementioned immunisation with collagen:

Regime 1: single dose of 7.5 my every third day for four doses,

Regime 2: single initial dose of 7.5 mg followed by daily doses of 1 mg per day for 14 days, Regime 3: single dose of 1.0 mg per day for 14 days, and Regime 4: single dose of 0.3 mg per day for 14 days.

As a control, untreated transgenic mice were examined 23 to 25 days after immunisation with collagen.

A standard arthritis scoring system index was used to measure the severity of the disease for the duration of the treatment period (up to 60 days). The mice were examined 3 times per week from day 14 to 36 after the first collagen injection. The severity of arthritis was rated on a scale from 0 to 3 for each limb based on the swelling, redness and joint function. The score (arthritis index) for each mouse was calculated as the sum of the score from the four limbs according to the following:

Score 0=normal

Score 1=mild swelling/redness

Score 2=severe swelling and redness

Score 3=severe swelling and redness accompanied by joint dysfunction.

Dose response studies were undertaken to determine the minimum effective dose of compound [153] that can effectively inhibit development of collagen induced arthritis. FIG. 2($a$) is a graph of Arthritis Index against time (in days) for treatment of FcγRIIa transgenic mice with compound [153] as compared with treatment with PBS. The mice were tested between 12 to 14 weeks of age with compound [153] according to abovementioned dosage Regimes 1 to 4. By comparison with the PBS dosing regime, all the dosage regimes were successful, Regime 1 being comparatively more effective than Regimes 1, 2 or 3. FIGS. 2(b) to 2(e) depict each of the individual dosage regimes depicted in FIG. 2(a) with the addition of error bars.

FIG. 3 is a graph of Arthritis Index against time in Days for treatment of control (non-transgenic) mice with compound [153]. The mice were tested between 12 to 14 weeks of age with compound [153] according to abovementioned dosage Regimes 3 and 4. As can be seen from the graph, the compound does not have a significant effect in non-transgenic mice implying specificity of action. Mice that have been treated in this way do not develop more severe arthritis upon cessation of treatment.

FIG. 4 is a graph of % Inhibition of IgG induced platelet activation against compound Concentration (mM) for nine of the compounds of the present invention, namely [216], [217], [261], [292], [294], [297], [299], [153] and [197]. The compounds were titrated and evaluated for capacity to prevent aggregated IgG induction of p-selectin expression as a measure of activation.

FIG. 5 is a graph of % Inhibition of Platelet Activation against compound Concentration (mM) for three of the compounds of the present invention, namely [113], [152] and [153].

FIG. 6 is a graph of % Inhibition of Platelet Activation against compound Concentration (mM) for four of the compounds of the present invention, namely [238], [239], [197] and [153].

FIGS. 4 to 6 showing the in vitro dose responses are, for the most part, only those compounds that have been through the entire selection program to the point where they would be ready for testing in vivo.

Preparative Examples

The present invention will be further illustrated with reference to the following examples of preparation of compounds according to the invention:

Preparation of 3-Isopropoxy-7-methoxy-N-(1H-1,2,3,4tetrazol-5-yl)-1-benzo[b]thiophene-2-carboxamide (VIB 090)

(a) 3-Chloro-5-methoxy-1-benzo[b]thiophene-2-carbonyl chloride and 3-chloro-7-methoxy-1-benzo[b]thiophene-2-carboxylate

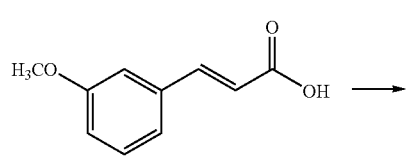

-continued

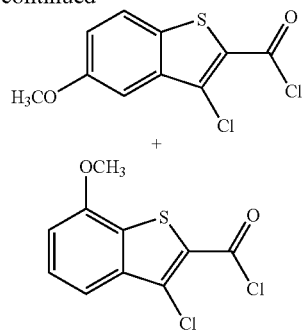

3-Methoxy cinnamic acid (5.0 mg, 28.06 mmol) was dissolved in anhydrous DMF (2.15 mL), chlorobenzene (40.0 mL) and pyridine (230.0 mL). To this solution was added thionyl chloride (10.5 mL) in a dropwise fashion at room temperature. The reaction mixture was heated to reflux for 24 hours. The reaction mixture was allowed to cool to room temperature and the solvents were evaporated under reduced pressure. Attempts to recrystallise the residue from t-BuOCH$_3$ and THF/hexane were unsuccessful. The residue was taken up in THF, filtered and evaporated under reduced pressure to afford a yellow solid, which was used without further purification in the next step.

(b) Isopropyl 3-isopropoxy-7-methoxy-1-benzo[b]thiophene-2-carboxylate

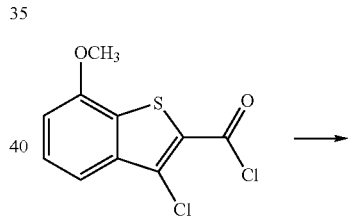

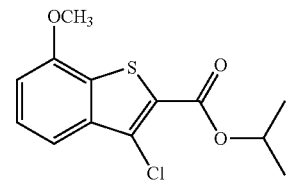

The crude mixture of 3chloro-5-methoxy-1-benzo[b]thiophene-2-carbonyl chloride and 3-chloro-7-methoxy-1-benzo[b]thiophene-2-carbonyl chloride (7.32 g, 28.06 mmol) was dissolved in THF (30.0 mL) and isopropanol (30.0 mL) and the reaction mixture was heated to reflux for 5 hours. The reaction mixture was then allowed to cool to room temperature, then concentrated under reduced pressure. T.L.C. (dichloromethane/hexane) (3/7) indicated 2 components, which were separated using column chromatography eluting with (dichloromethane/hexane) (3/7) to afford (483.0 mg, 6.0%) of the desired isopropyl 3-isopropoxy-7-methoxy-1-benzo[b]thiophene-2-carboxylate as a white powder, which was further purified by recrystallisation from hexane and (1.39 g, 17.0%) of isopropyl 3-isopropoxy-5-methoxy-1-benzo[b]thiophene-2-carboxylate.

(c) Isopropyl 3isopropoxy-7-methoxy-1-benzo[b]thiophene-2-carboxylate

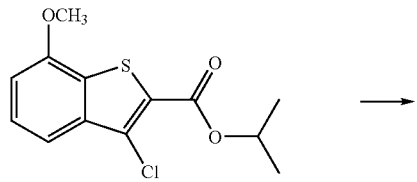

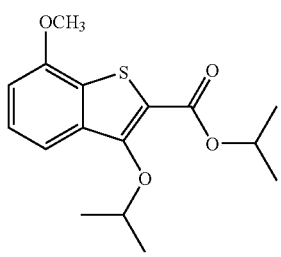

Isopropanol (2.0 mL) was added to a suspension of sodium hydride (60% dispersion, 110.0 mg, 2.75 mmol) and the reaction mixture was stirred at room temperature for 90 minutes. Isopropyl 3-chloro-7-methoxy-1-benzo[b]thiophene-2-carboxylate (400.0 mg, 1.4 mmol) was dissolved in anhydrous THF (2.0 mL) and the solution was added to the sodium hydride suspension and the resulting reaction mixture was heated to reflux for 17 hours. The reaction mixture was allowed to cool and the reaction mixture was concentrated under reduced pressure. The resulting residue was partitioned between hexane and water. The aqueous phase was extracted with hexane and the combined hexane extracts were dried, filtered and evaporated under reduced pressure to afford (433.0 mg, 99.9%) of the desired isopropyl 3-isopropoxy-7-methoxy-1-benzo[b]thiophene-2-carboxylate as a viscous yellow oil. M.S. m/z 308 (M)$^+$.

(d) 3-Isopropoxy-7-methoxy-1-benzo[b]thiophene-2-carboxylic acid

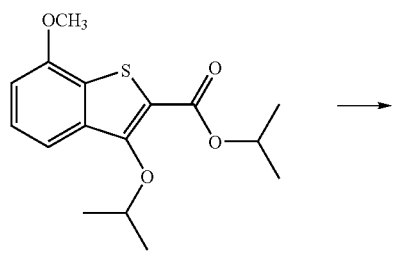

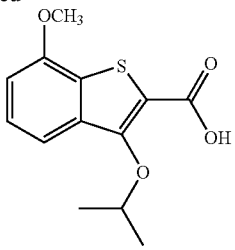

Isopropyl 3-isopropoxy-7-methoxy-1-benzo[b]thiophene-2-carboxylate (433.3 mg, 1.4 mmol) was dissolved in methanol (3.0 mL) and aqueous 1N sodium hydroxide solution (7.0 mL) was added and the reaction mixture was heated to reflux for 7 hours. The reaction mixture was allowed to cool then poured into water (30.0 mL) and the aqueous reaction mixture was acidified with concentrated hydrochloric acid and extracted with dichloromethane. The dichloromethane phase was dried, filtered and evaporated under reduced pressure to afford an off-white residue, which was recrystallised from methanol/water to afford (99.9 mg, 36.1%) of the desired 3-isopropoxy-7-methoxy-1-benzo[b]thiophene-2-carboxylic acid as fine white crystals. M.S. m/z 260 (M−1)$^+$.

(e) 3-Isopropoxy-7-methoxy-N-(1H-1,2,3,4tetrazol-5-yl)-1-benzo[b]thiophene-2-carboxamide (VIB 090).

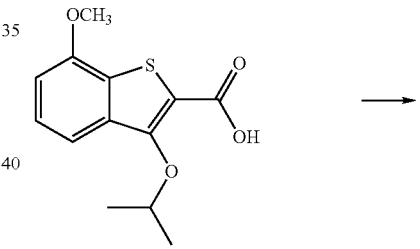

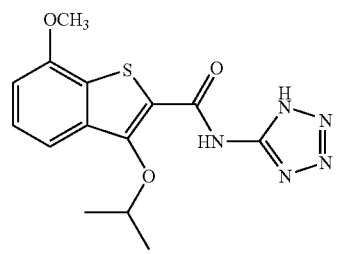

3-Isopropoxy-7-methoxy-1-benzo[b]thiophene-2-carboxylic acid (70.0 mg, 0.26 mmol) was dissolved in anhydrous THF (2.0 mL) and CDI (55.0 mg, 0.34 mmol) was added and the reaction mixture was heated to reflux for 75 minutes. The reaction mixture was allowed to cool and 5-amino tetrazole (25.0 mg, 0.3 mmol) was added and the reaction mixture was heated to reflux overnight. The reaction mixture was allowed to cool and then poured into water (30.0 mL). The aqueous reaction mixture was acidified with concentrated hydrochloric acid and a precipitate formed and was collected by filtration, washed well with water, dried and recrystallised from methanol/water to afford (74.3 mg, 85.0%) of the desired 3-isopropoxy-7-methoxy-N-(1H-1,2,3,4-tetrazol-5-yl)-1-benzo[b]thiophene-2-carboxamide (VIB 090) as yellow needles. M.S. m/z 332 (M−1)+.

Preparation of 3-Isopropoxy-4nitro-5-methoxy-N-(1H-1,2,3,4-tetrazol-5-yl)-1-benzo[b]thiophene-2-carboxamide (VIB-092)

(a) 3-Chloro-5-methoxy-1-benzo[b]thiophene-2-carbonyl chloride

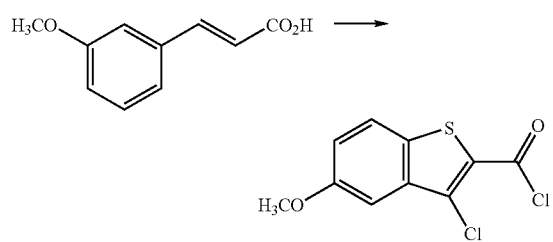

3-Methoxy cinnamic acid (5.0 g, 28.0 mmol) was added to anhydrous pyridine (230.0 mL) and anhydrous N,N-dimethylformamide (2.15 mL) and anhydrous chlorobenzene (40.0 mL) and thionyl chloride (10.5 mL, 0.14 mol) was then added dropwise and the reaction mixture was heated to reflux for 24 hours. The reaction mixture was cooled and the solvent evaporated under reduced pressure. Attempts to recrystallise the residue from t-BuOCH$_3$ and (THF/hexane) were unsuccessful. As such the residue was redissolved in THF, filtered and the THF was evaporated under reduced pressure to afford (7.0 g, 97.0%) of the desired 3-chloro-5-methoxy-1-benzo[b]thiophene-2-carbonyl chloride as a yellow solid. M.S. m/z 260 (M)+. $^1$H NMR (CDCl$_3$) δ 3.73 (3H, s, OCH$_3$), 3.93 (3H, s, OCH$_3$), 6.9 (1H, m, ArH), 7.05 (1H, s, ArH), 7.6 (1H, m, ArH).

(b) Isopropyl 3-chloro-5-methoxy-1-benzo[b]thiophene-2-carboxylate

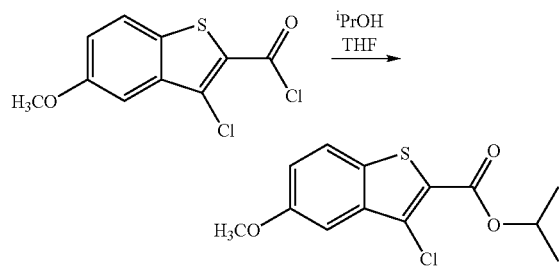

3-Chloro-5-methoxy-1-benzo[b]thiophene-2-carbonyl chloride (7.32 g, 28.1 mmol) was dissolved in a solution of anhydrous THF (30.0 mL) and isopropanol (30.0 mL) was added and the reaction mixture was heated to reflux for 5 hours. The reaction mixture was allowed to cool and the solvent evaporated under reduced pressure to afford a residue which was purified by column chromatography eluting with (dichloromethane/hexane) (3/7) to afford (1.39 g, 17.0%) of the desired isopropyl 3-chloro-5-methoxy-1-benzo[b]thiophene-2-carboxylate as a white powder. m.p.=76-80° C., M.S. m/z 285 (M+1)+. $^1$H NMR (CDCl$_3$) δ 1.33 (6H, d, CH(CH$_3$)$_2$, J=6.24 Hz), 3.85 (3H, s, OCH$_3$), 5.21 (1H, m, CH(CH$_3$)$_2$, J=6.24 Hz), 7.09 (1H, dd, ArH, J=2.49, 8.85 Hz), 7.26 (1H, d, ArH, J=2.46 Hz), 7.59 (1H d, ArH, J=8.85 Hz).

(c) Isopropyl 3-isopropoxy-5-methoxy-1-benzo[b]thiophene-2-carboxylate

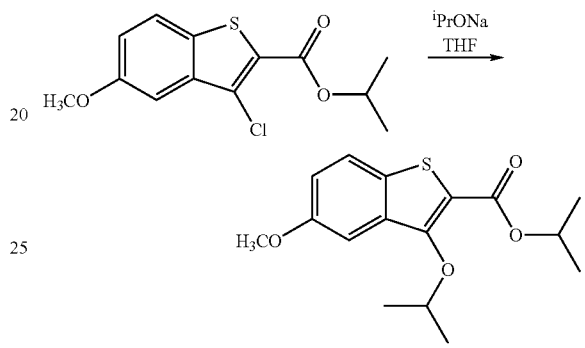

Sodium hydride (60% dispersion) (600.0 mg, 4.0 mmol) was suspended in anhydrous THF (2.0 mL) and stirred at room temperature under an atmosphere of nitrogen for 2 minutes. A solution of isopropanol (350.0 mL, 4.6 mmol) dissolved in anhydrous THF (2.0 mL) was slowly added to the sodium hydride in THF. The reaction mixture was stirred at room temperature for 1.5 hours, then a solution of isopropyl 3-chloro-5-methoxy-1-benzo[b]thiophene-2-carboxylate (600.0 mg, 2.1 mmol) in anhydrous THF (3.0 mL) was slowly added. The resultant reaction mixture was heated to reflux for 17 hours. The reaction mixture was cooled and the THF was evaporated under reduced pressure and the remaining residue was partitioned between hexane and water. The aqueous phase was extracted with hexane and the hexane phase was dried, filtered, and evaporated under reduced pressure to afford the desired isopropyl 3-isopropoxy-5-methoxy-1-benzo[b]thiophene-2-carboxylate as a viscous yellow oil. M.S. m/z 309 (M+1)+. $^1$H NMR (CDCl$_3$) δ 1.24 (6H, d, 2×CH$_3$, J=3.84 Hz), 2.1 (6H, s, 2×CH$_3$, J=6.9 Hz), 3.89 (3H, s, OCH$_3$), 7.05 (1H, ArH, J=11.1 Hz).

(d) 3-Isopropoxy-5methoxy-1-benzo[b]thiophene-2-carboxylic acid

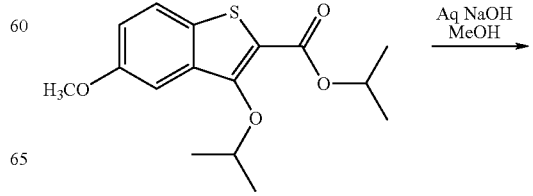

-continued

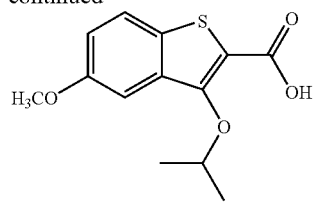

Isopropyl 3-isopropoxy-5-methoxy-1-benzo[b]thiophene-2-carboxylate (649.0 mg, 2.1 mmol) was dissolved in methanol (2.5 mL) and aqueous 1N sodium hydroxide (7.0 mL) was added and the reaction mixture was heated to reflux for 7 hours. The reaction mixture was allowed to cool and the reaction mixture was poured into water. The aqueous solution was then extracted with dichloromethane and the aqueous phase was acidified and extracted with dichloromethane. The dichloromethane extracts of the acidified aqueous phase were combined, dried, filtered and evaporated under reduced pressure to afford a residue, which was recrystallised from acetonitrile to afford (148.0 g, 25.0%) of the desired 3-isopropoxy-5-methoxy-1-benzo[b]thiophene-2-carboxylic acid as pale yellow fluffy crystals. m.p.=76-80° C., M.S. m/z 284 (M)$^+$. $^1$H NMR (CDCl$_3$) δ 3.85 (3H, s, OCH$_3$), 7.09 (1H, dd, ArH, J=2.49, 8.85 Hz), 7.26 (1H, d, ArH, J=2.46 Hz), 7.59 (1H, d, ArH, J=8.85 Hz). Found C, 54.53, H, 4.58%, C$_{13}$H$_{13}$ClO$_3$S requires C, 54.93, H, 4.53%. H.P.L.C. retention time=5.37 minutes. Linear Gradient over 10 minutes. 10 B/90 D to 90 B/10D (B=90% CH$_3$CN/10% H$_2$O), (D=0.1N NH$_4$OAc (pH=4)).

(e) 3-Isopropoxy-4-nitro-5-methoxy-1-benzo[b]thiophene-2-carboxylic acid

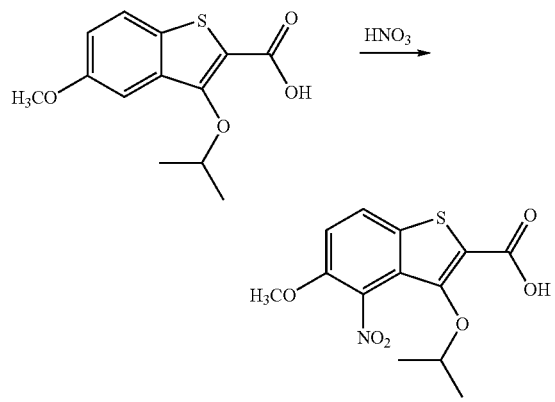

3-Isopropoxy-5-methoxy-1-benzo[b]thiophene-2-carboxylic acid (200.0 mg, 0.75 mmol) was added to acetic acid (5.0 mL) and concentrated nitric acid (1.0 mL) and the reaction mixture was stirred at between 0 and 5° C. in an icebath for 66 minutes. The yellow solution was poured into water (75.0 mL) and the yellow precipitate was collected by filtration, washed well with water and dried to afford a yellow powder, which was recrystallised from (dichloromethane/hexane) to afford (129.0 mg, 55.0%) of the desired 3-isopropoxy-4-nitro-5-methoxy-1-benzo[b]thiophene-2-carboxylic acid as yellow crystals. m.p.=197-200 □C, M.S. m/z 312 (M+1)$^+$. $^1$H NMR (CDCl$_3$) δ 1.32 (6H, d, CH(CH$_3$)$_2$, J=6.09 Hz), 3.99 (3H, s, CH$_3$), 5.02 (1H, m, CH(CH$_3$)$_2$, J=6.12 Hz), 7.32 (1H, d, ArH, J=9.0 Hz), 7.81 (1H, d, ArH, J=8.97 Hz). Found C, 50.13, H, 4.17, N, 4.42%, C$_{13}$H$_{13}$NO$_6$S requires C, 50.16, H, 4.21, N, 4.5%. H.P.L.C. retention time=6.39 minutes. 10 B/90 D to 90 B/10D (B=90% CH$_3$CN/10% H$_2$O), (D=0.1N NH$_4$OAc (pH=4)).

(f) 3-Isopropoxy-4nitro-5-methoxy-N-(1H-1,2,3,4-tetrazol-5-yl)-1-benzo[b]thiophene-2-carboxamide (VIB-092).

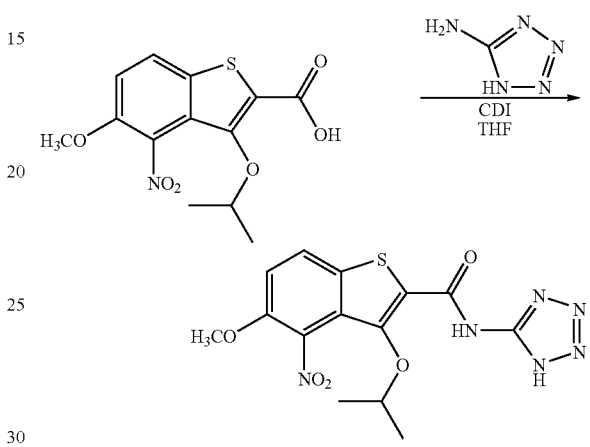

3-Isopropoxy-4-nitro-5-methoxy-1-benzo[b]thiophene-2-carboxylic acid (100.0 mg, 0.32 mmol) was dissolved in anhydrous THF (2.0 mL) and CDI (62.0 mg, 0.38 mmol) was added and the reaction mixture was heated to reflux for 90 minutes. The reaction mixture was allowed to cool and 5-amino tetrazole (30.0 mg, 0.35 mmol) was added and the reaction mixture was heated to reflux for a further 4 hours. The reaction mixture was allowed to cool and a yellow precipitate formed and was collected by filtration, washed well with water and dried to afford (50.0 mg, 41.0%) of the desired 3-isopropoxy-4-nitro-5-methoxy-N-(1H-1,2,3,4-tetrazol-5-yl)-1-benzo[b]thiophene-2-carboxamide (VIB-092) as a yellow powder. m.p.=236-238° C., M.S. m/z 378 (M+1)$^+$. $^1$H NMR (DMSO-d$_6$) δ 1.15 (6H, d, CH(CH$_3$)$_2$, J=6.06 Hz), 3.97 (3H, s, OCH$_3$), 4.5 (1H, m, CH(CH$_3$)$_2$, J=6.03 Hz), 7.64 (1H, d, ArH, J=9.12 Hz), 8.25 (1H, d, ArH, J=9.09 Hz). Found C, 55.62, H, 5.09, N, 4.94, %, C$_{13}$H$_{15}$NO$_4$S requires C, 55.5, H, 5.37, N, 4.98%. Found (M+1)$^+$.=282.08002 C$_{13}$H$_{15}$NO$_4$S requires (M+1)$^+$.=282.08000.

Preparation of 3-(2-Hydroxyphenyl) buten-2-oic acid (VIB 297)

(a) 5-(-Methyl-3-hydroxybenzylidine)rhodanine

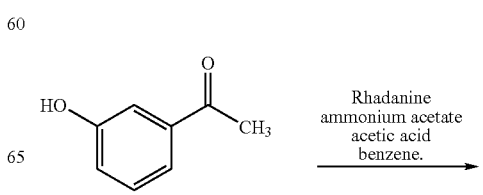

-continued

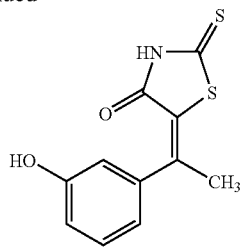

Rhodanine (2.0 g, 15.0 mmol), was added to a stirred solution of ammonium acetate (120.0 mg) and glacial acetic acid (360.0 mL) in benzene (13.0 mL). The reaction mixture was stirred to boiling for 5 minutes. 3-Hydroxyacetophenone (2.0 g, 145.7 mmol) was then added to the reaction mixture and the flask was connected to a Dean Stark trap. The reaction mixture was then heated to reflux overnight, then allowed to cool to room temperature after which a yellow precipitate formed. The precipitate was then collected by filtration, washed with water and purified by recrystallisation from (methanol/water) to afford (2.17 g, 59.0%) of the desired product as a yellow powder. M.p.=201-202° C., M.S. m/s 252 (M+1)+. $^1$H NMR (DMSO) δ 2.51 (6H, d, CH(CH$_3$)$_2$, J=6.18 Hz), 3.40 (3H, s, OCH$_3$), 3.88 (3H, s, SO$_2$CH$_3$), 4.94 (1H, pent, CH(CH$_3$)$_2$, J=6.18 Hz), 7.12-7.16 (2H, m, 2×ArH), 7.66 (1, d, ArH, J=5.61 Hz), 9.98 (1H, s, NH).

(b) 3-(2-Hydroxyphenyl) buten-2-oic acid. (VIB-297)

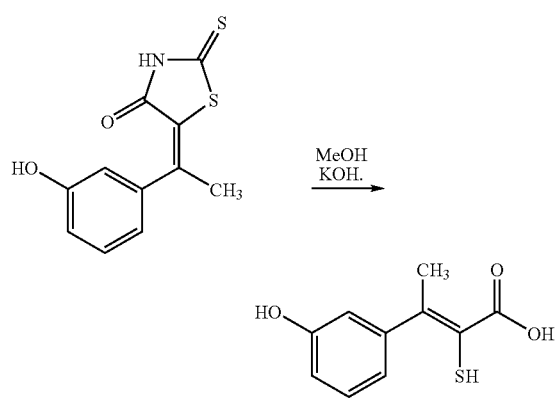

5-(-Methyl-3-hydroxybenzylidine)rhodanine (300.0 mg, 1.2 mmol), was added to a stirred solution of potassium hydroxide (340.0 mg, 6.0 mmol) in methanol (20.0 mL). The reaction mixture was stirred at room temperature for 2 hours. The reaction mixture was then slowly acidified with glacial acetic acid. The yellow precipitate was collected by filtration and purified by recrystallisation from propanol to afford (241.0 mg, 97.9%) of the desired product (VIB 297) as yellow crystals. M.S. m/s 211 (M+1)+. $^1$H NMR (DMSO) δ 2.51 (6H, d, CH(CH$_3$)$_2$, J=6.18 Hz), 3.4 (3H, s, OCH$_3$), 3.88 (3H, s, SO$_2$CH$_3$), 4.94 (1H, pent, CH(CH$_3$)$_2$, J=6.18 Hz), 7.12-7.16 (2H, m, 2×ArH), 7.66 (1H, d, ArH, J=5.61 Hz), 9.98 (1H, s, NH).

Preparation of 3-Cyclohexyloxy-5-methoxy-1-benzo[b]thiophene-2-carboxylic acid (VIB-276)

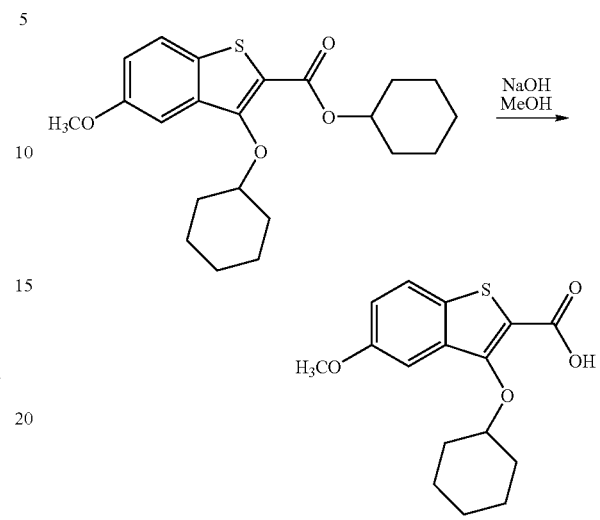

Cyclohexyl 3-cyclohexyloxy-5-methoxy-1-benzo[b]thiophene-2-carboxylate (3.0 g, 7.72 mmol) was dissolved in methanol (60.0 mL) and water (15.0 mL) and sodium hydroxide (8.0 g, 0.2 mol) was added and the reaction mixture was heated to reflux for 17.0 hours. A colourless fluffy solid precipitated. The reaction mixture was allowed to cool and the precipitate was collected by filtration and then stirred with 1N aqueous hydrochloric acid (50.0 mL) and the resulting solid was collected by filtration and purified by recrystallisation from methanol/water to afford (2.3 g, 97.2%) of the desired 3-cyclohexyloxy-5-methoxy-1-benzo[b]thiophene-2-carboxylic acid as small white crystals. m.p.=176-177° C., M.S. m/z 307 (M+1)+. $^1$H NMR (CDCl$_3$) δ1.26-1.40 (6H, m, 3×CH), 1.61-1.73 (3H, m, 3×CH), 1.84-1.88 (2H, m, 2×CH), 2.11-2.15 (2H, m, 2×CH), 3.91 (3H, s, OCH$_3$), 4.56 (1H, m, CH(CH$_3$)$_2$, J=4.08 Hz), 7.16 (1H, dd, ArH, J=2.49, 8.85 Hz), 7.26 (1H, m, ArH), 7.65 (1H, d, ArH, J=5.01 Hz). Found C, 62.62, H, 5.98%. C$_{16}$H$_{18}$O$_4$S requires C, 62.72, H, 5.92%. H.P.L.C. retention time=6.56 minutes. (10% B/90% D) to (90% B/10% D) over 20 minutes (B=90% CH$_3$CN 10% H$_2$O) (D=0.1N NH$_4$OAc (pH=4).

Preparation of 3-Chloro-6-nitro-1-benzo[b]thiophene-S-oxo-2-carboxylic acid (VIB-044)

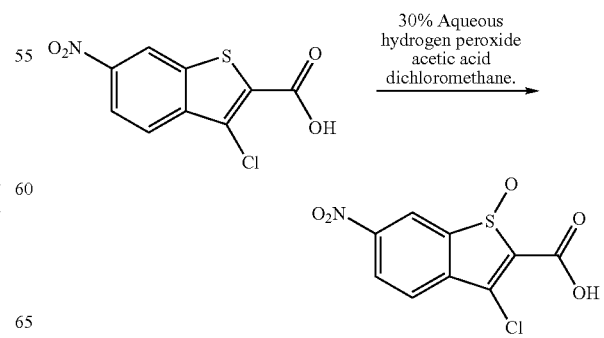

30% Aqueous hydrogen peroxide (9.2 mL, 81.0 mmol) was added to 3-chloro-6-nitro-1-benzo[b]thiophene-2-carboxylic acid (500.0 mg, 1.94 mmol) dissolved in acetic acid (19.3 mL) and the reaction mixture was stirred at room temperature for 24 hours. The reaction mixture was diluted with water and the aqueous phase was extracted with dichloromethane and the dichloromethane phase was washed with brine, water and saturated aqueous NaHCO₃ solution. The dichloromethane phase was then dried, filtered and evaporated under reduced pressure to afford an off white solid, which was purified by column chromatography eluting with (ethyl acetate/hexane/acetic acid) (40/40/10) to afford the desired 3-chloro-6-nitro-1-benzo[b]thiophene-S-oxo-2-carboxylic acid.

Preparation of
3-Chloro-6nitro-1-benzo[b]thiophene-2-carboxylic
add (V.I.B-026)

(a) Methyl 3-chloro-6-nitro-1-benzo[b]thiophene-2-carboxylate)

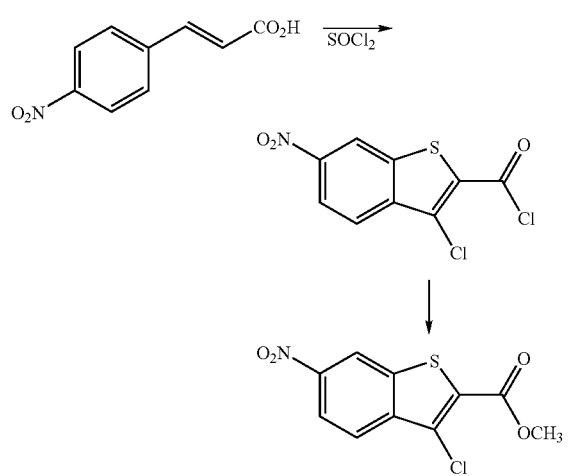

4-Nitro cinnamic acid (10.0 g, 52.0 mmol) was dissolved in anhydrous DMF (4.0 mL) and chlorobenzene (70.0 mL) and anhydrous pyridine (410.0 mL) was added. To this reaction mixture thionyl chloride (19.0 mL, 260.0 mmol) was added dropwise over 30 minutes at room temperature. The reaction mixture was heated at reflux for 24 hours. A precipitate formed after about 3 hours and the reaction mixture gradually became a brown colour. The reaction mixture was allowed to cool to room temperature and then to about 0° C. in ice. The precipitate was collected by filtration, washed well with diethyl ether and dried to afford (6.0 g, 44.0%) of the desired 3-chloro4-nitro-1-benzo[b]thiophene-2-carbonyl chloride. The 3-chloro-6-nitro-1-benzo[b]thiophene-2-carbonyl chloride (6.0 g, 22.0 mmol) was suspended in anhydrous THF (180.0 mL) and methanol (120.0 mL) was added dropwise over 1 hour and the greenish suspension was stirred for 6 hours. The solvent was evaporated under reduced pressure and the residue was subject to rapid silica filtration eluting with dichloromethane. The yellow eluent was evaporated under reduced pressure and the yellow residue was purified by recrystallisation from ethyl acetate to afford (5.2 g, 37.0%) of the desired methyl 3-chloro-6-nitro-1-benzo[b]thiophene-2-carboxylate as dark yellow/green prisms. m.p.=216-217° C., M.S. m/z 271 (M+1)⁺. ¹H NMR (CDCl₃) δ 4.0 (3H, s, OCH₃), 8.12 (1H, d, ArH J=8.94 Hz), 8.35 (1H, dd, ArH, J=1.92, 8.91 Hz), 8.78 (1H, d, ArH, J=1.89 Hz). Found C, 44.18, H, 2.19, N, 5.19%, C₁₀H₆ClNO₄S requires C, 44.28, H, 2.21, N, 5.17%.

(b) 3-Chloro-6-nitro-1-benzo[b]thiophene-2-carboxylic acid (V.I.B-026)

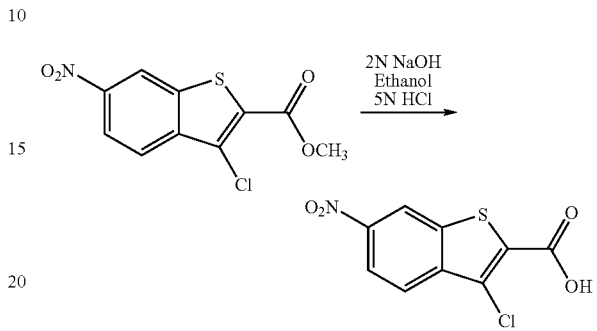

Methyl 3-chloro-6-nitro-1-benzo[b]thiophene-2-carboxylate (46.2 mg, 0.17 mmol) was dissolved in ethanol (2.0 mL) and aqueous 2N NaOH (0.5 mL) was added. The reaction mixture was heated to reflux for 1.0 hour and then allowed to cool to room temperature and stirred at room temperature for 48 hours. The solvent was evaporated under reduced pressure to afford a white residue which was taken up in water and acidified, then extracted with ethyl acetate, dried and evaporated under reduced pressure to afford a (30.0 mg, 68.7%) of the desired 3-chloro-6-nitro-1-benzo[b]thiophene-2-carboxylic acid as white powder. M.S. m/z 255.71 (M−1)⁺. ¹H NMR (300.13, d₆-DMSO) δ 8.14 (1H, m, ArH), 8.35 (1H, m, ArH), 9.20 (1H, m, ArH).

Preparation of
3-[(3-Carboxyphenyl)sulfinyl]benzenecarboxylic
acid (V.I.B-032)

(a) 3-[(Carboxyphenyl)sulfanyl]benzenecarboxylic
acid. (V.I.B-006)

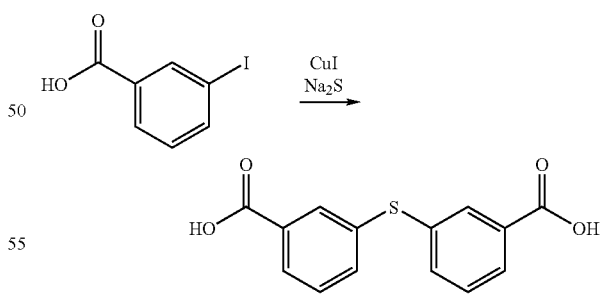

To a solution of 3-iodobenzoic acid (24.8 g, 100.0 mmol) was dissolved in anhydrous DMF (100.0 mL) was added potassium carbonate (6.9 g, 50.0 mmol). The reaction mixture was heated to 100° C. for 5 minutes and sodium sulphide (4.3 g, 55.0 mmol) and copper iodide (1.9 g, 10.0 mmol) was added and the reaction mixture was heated to reflux under an atmosphere of nitrogen for 12 hours. Water (500.0 mL) was then added and the reaction mixture was heated to boiling with activated carbon. The carbon was filtered off while hot into an excess of 6N HCl (50.0 mL). A precipitate formed on cooling to room temperature and was collected by filtration and washed with water to afford (5.36 g, 19.5%) of the desired 3-[(carboxyphenyl)sulfanyl]benzenecarboxylic acid (GM71/7) as an off-white powder. M.S. m/z 272.73 (M−1)+. $^1$H NMR (300.13, $d_6$-DMSO) 7.32-7.63 (4H, m, 4×ArH), 7.84-7.99 (4H, m, 4×ArH).

(b) 3-[(3-Carboxyphenyl)sulfinyl]benzenecarboxylic acid (V.I.B-032)

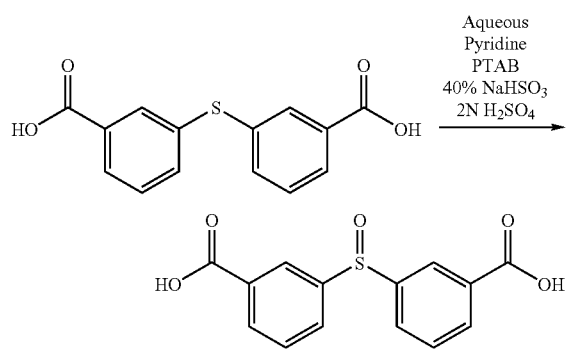

To a stirred ice cooled solution of 3-[(carboxyphenyl)sulfanyl]benzenecarboxylic acid (GM71/7, VIB-006) (1.0 g, 3.65 mmol) in aqueous pyridine ((1/1) 5.84 mL), phenyl trimethylammonium tribromide (1.43 g, 3.8 mmol) was gradually added in portions to keep the temperature between 0 and 10° C. When addition was complete, the reaction mixture was stirred at room temperature for 24 hours. Then the unreacted PTAB was decomposed with 40% NaHSO$_3$ (3.65 mL). Ice water (14.6 mL) was then added and the reaction mixture was acidified with 2N H$_2$SO$_4$. A solid precipitated to afford (833.0 mg, 78.7%) of the desired 3-[(3-Carboxyphenyl)sulfinyl]benzenecarboxylic acid (GM71/21, VIB-032) as a white powder. M.S. m/z 288.70 (M−1)+. $^1$H NMR (300.13, $d_6$-DMSO) 7.67 (2H, t, 2×ArH, J=7.8 Hz), 7.99 (4H, m, 4×ArH), 8.23 (2H, m, 2×ArH). $^1$H NMR (300.13, $d_6$-DMSO) 38.8, 132.2, 133.1, 133.4, 139.5. Found C, 53.97, H, 3.22%, $C_{14}H_{10}O_5S \cdot 1.0\ H_2O$ requires C, 54.49, H, 3.24%.

(Reference: Rabai, J., Kapovits, I., Tanacs, B and Tamas, J., *Synthesis*, 1990, 847-849.

Preparation of 3-(2-Oxophenylethylsulfanyl)benzoic acid (VIB-294)

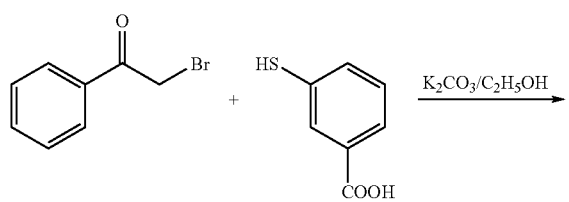

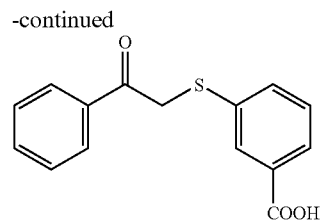

To bromoacetophenone (250 mg, 1.16 mmole) and anhydrous K$_2$CO$_3$ (694 mg, 5.02 mmole) in ethanol, 193.6 mg (1.25 mmole) 3-mercaptobenzoic acid was added and the mixture refluxed overnight. The solvent was evaporated and water added to the solid residue. The basic aqueous solution was extracted with ethyl acetate to remove unreacted bromoacetophenone. The aqueous layer was acidified and extracted with ethyl acetate, dried, evaporated and the residue purified by flash chromatography using chloroform:methanol 95:5. Evaporation of the fractions resulted in a yellow powder (380 mg). M.S. m/s 271 (M−1)+. $^1$H NMR (DMSO) δ4.75 (2H, s, —CH2-), 7.39-7.7 (4H, m, 4×ArH), 7.75 (1H, d, ArH, J=5.61 Hz), 7.86 (1H, s, ArH), 8.02 (3H, d, ArH).

Preparation of 3-[2-(3-Cyanophenyl)-2-oxoethylsulfanyl]benzoic acid (VIB 216)

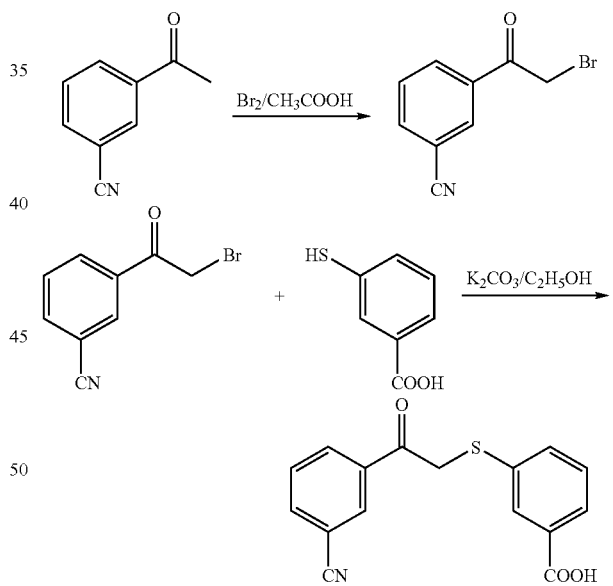

3-acetylbezonitrile (2.5 g, 0.017 mole) was dissolved in acetic acid (50 ml) then bromine liquid (3 gm, 0.0187 mole) in acetic acid (12.5 ml) was added dropwise over 2 hrs. The reaction mixture was stirred overnight. The acetic acid was evaporated to yield a fawn coloured solid (3.63 gm). This was used in the next step without further purification.

Bromoacetylbenzonitrile (300 mg, 1.34 mmole) and anhydrous K$_2$CO$_3$ (740 mg, 5.35 mmole) in ethanol, 210 mg (1.36 mmole) 3-mercaptobenzoic acid was added and the mixture refluxed overnight. The solvent was evaporated and water added to the solid residue. The basic aqueous solution was extracted with ethyl acetate to remove unreacted-bromoacetylbenzonitrile. The aqueous layer was acidified and extracted with ethyl acetate, dried, evaporated and the residue purified by flash chromatography using chloroform followed by chloroform:methanol (99:1). Evaporation of high Rf yellow fractions resulted in a yellow powder (130 mg). M.S. m/s 296 (M−1)+. $^1$H NMR (DMSO) δ 4.31 (2H, s, —CH2-), 7.25-8.25 (8H, m, 8×ArH).

2-[3-Oxo-3-(1H-pyrrol-2-yl)propenyl]benzoic acid (VIB 238)

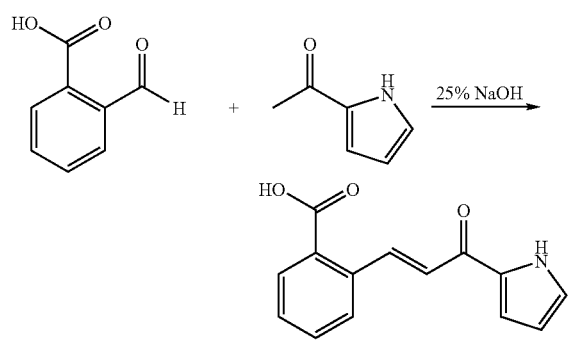

1 gm (6.7 mmole) 2-carboxybenzaldehyde and 2-acetylindole (726.8 mg, 6.7 mmole) were dissolved in absolute ethanol (16 ml) and NaOH (25%, 16 ml) was added and stirred overnight. The reaction mixture was added to water and extracted with ethyl acetate to remove unreacted 2-acetylindole. The aqueous solution was acidified and extracted with ethyl acetate. The ethyl acetate extract was wased with water, dried and evaporated to yield the chalcone (1.28 gm).

Preparation of 3-(3-Cyanopropylsulfanyl)benzoic acid (VIB 239)

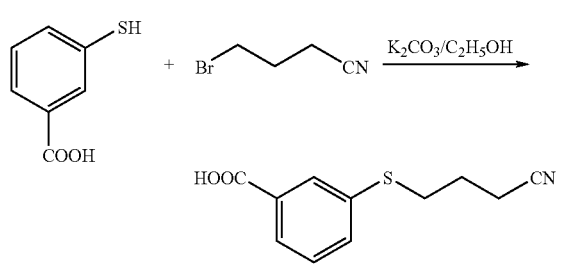

To solution of 3-mercaptobenzoic acid (250 mg, 1.62 mmole) in ethanol (10 ml), anhydrous potassium carbonate (896 mg, 6.48 mmole) was added followed by bromobutyronitrile (239.97 mg, 1.62 mmole). The reaction mixture was refluxed overnight. The ethanol was evaporated and water added. The basic solution was extracted with ethyl acetate. The aqueous layer was acidified and the resulting precipitate filtered and dried to yield 196 mg product. M.S. m/s 220 (M−1)+. $^1$H NMR (DMSO) δ 1.79 (2H, m, —CH2-), 2.37 (2H, t, —CH2-), 3.02 (2H, t, CH2), 7.56 (1H, d, 1×ArH), 7.74 (1H, d, 1×ArH), 7.83 (1H, bs, 1H, 1×ArH).

Preparation of 3-[2-Oxo-2-(3-carboxyphenyl)ethylsulfanyl]benzoic acid (VIB 217)

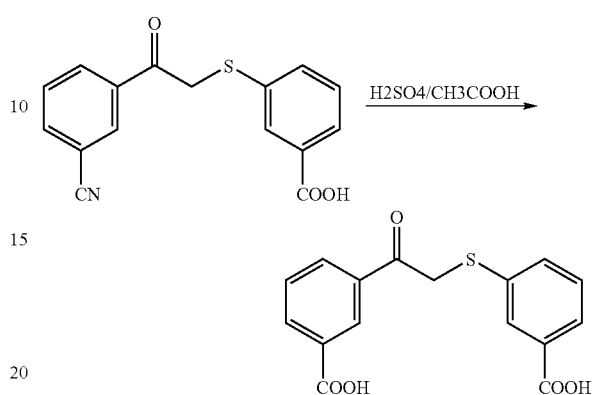

The nitrile (VIB 216) (100 mg, 0.316 mmole) was dissolved in acetic acid (3 ml), conc sulphuric acid (1 ml) and water (1 ml) and the mixture refluxed overnight. A precipitate formed overnight. The mixture was added to water and extracted with ethyl acetate. The ethyl acetate extract was washed with water, dried and evaporated to yield the product (50 mg). M.S. m/s 314 (M−2)+. $^1$H NMR (DMSO) δ 4.57 (2H, s, —CH2-), 7.3-8.6 (8H, m, 8×ArH).

Preparation of 1-(3-Carboxyphenyl)-2-[2-(3-carboxyphenyl)-2-oxoethylsulfanyl]ethanone (VIB 292)

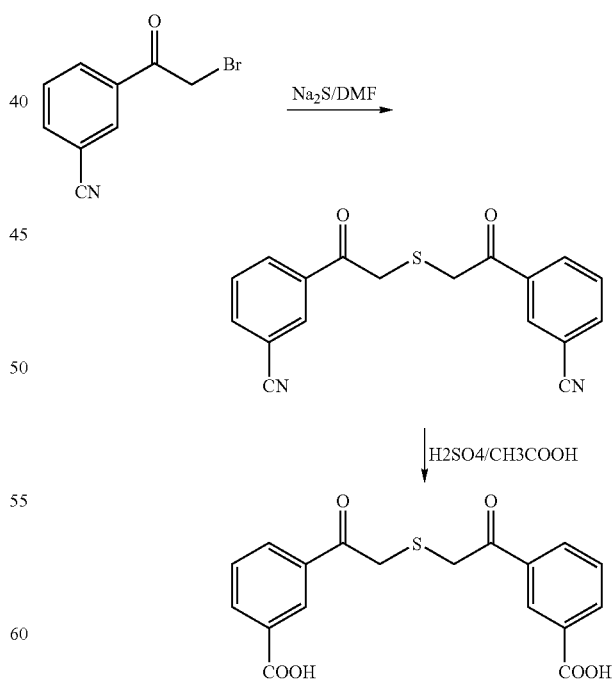

To a suspension of sodium sulphide (100 mg, 1.28 mmole) in DMF (5 ml) was added 3-bromoacetylbenzonitrile (500 mg, 2.23 mmole) in DMF (2 ml) and the mixture stirred overnight. The DMF was evaporated and water added to the residue. The mixture was extracted with dichloromethane and the extract washed with water, dried and evaporated to yield a brown oil which was used in the next step without purification.

The dinitrile (440 mg) was dissolved in acetic acid (6 ml), conc sulphuric acid (2 ml) and water (2 ml) and refluxed overnight. A precipitate formed. The mixture was added to water and the brown solid filtered and dried to yield product (200 mg). M.S. m/s 356 (M−2)+. $^1$H NMR (DMSO) δ 4.24 (4H, s, 2×—CH2-), 7.2-8.6 (8H, m, 8×ArH).

Preparation of 4-[(2-oxo-2-phenylethyl)thio]benzoic acid (VIB-384)

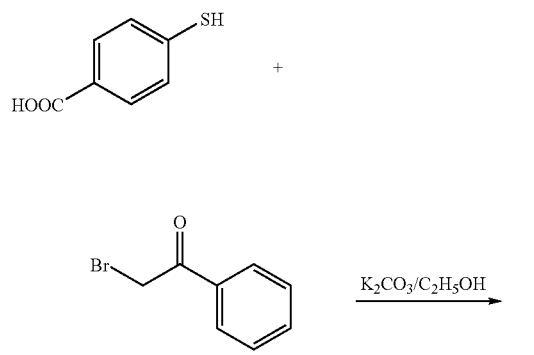

To bromoacetophenone (322.8 mg, 1.62 mmole) and anhydrous $K_2CO_3$ (896 mg, 6.48 mmole) in ethanol (20 ml), 250 mg (1.62 mmole) 4-mercaptobenzoic acid was added and the mixture refluxed overnight. The solvent was evaporated and water added to the solid residue. The basic aqueous solution was extracted with ethyl acetate to remove unreacted bromoacetophenone. The aqueous layer was acidified to yield a precipitate which was filtered and dried (356 mg). m/z 271 (M−1)+1H NMR (DMSO) δ 4.75 (2H, s, —CH2-), 7.35-7.72 (5H, m, 5×ArH), 7.82 (2H, d, 2×ArH), 8.05 (2H, d, 2×ArH).

Preparation of 4-{[2-(3-cyanophenyl)-2-oxoethyl]thio}benzoic acid (VIB 385)

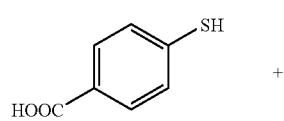

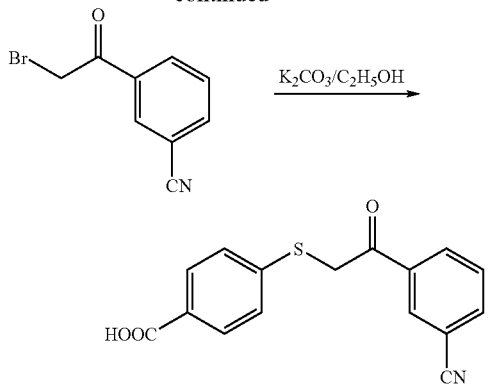

To 3-cyanobromoacetophenone (363.3 mg, 1.62 mmole) and anhydrous K2CO3 (896 mg, 6.48 mmole) in ethanol (20 ml), 250 mg (1.62 mmole) 4-mercaptobenzoic acid was added and the mixture refluxed overnight. The solvent was evaporated and water added to the solid residue. The basic aqueous solution was extracted with ethyl acetate to remove unreacted bromoacetophenone. The aqueous layer was acidified to yield a precipitate which was filtered and dried (377 mg). The solid was further purified by flash chromatography (CHCl3:CH3OH 99:1 to 95:5. The homogeneous fractions were pooled and evaporated to yield product (110 mg). m/z 296 (M−1)+$^1$HNMR (DMSO) δ 4.9 (2H, s, —CH2-), 7.44 (2H, d, 2×ArH), 7.63 (1H, d, ArH), 7.76 (1H, t, ArH), 7.83 (2H, d, 2×ArH), 7.93 (1H, d, ArH), 8.13 (1H, d, ArH), 8.29 (1H, d, ArH), 8.54 (1H, d, ArH).

Preparation of 2-{[2-(4-carboxyphenyl)-2-oxoethyl]thio}benzoic acid (VIB 410)

To bromoacetophenone (394.09 mg, 1.62 mmole) and anhydrous $K_2CO_3$ (896 mg, 6.48 mmole) in ethanol (20 ml), 250 mg (1.62 mmole) 2-mercaptobenzoic acid was added and the mixture refluxed overnight. The solvent was evaporated and water added to the solid residue. The aqueous layer was acidified to yield a precipitate which was filtered and dried (487 mg). m/z 315 (M−1)+$^1$HNMR (DMSO) δ 4.75 (s, 2H, —CH2-), 7.22 (1H, t, ArH), 7.47 (2H, t, 2×ArH), 7.87 (1H, d, ArH), 8.06 (2H, d, 2×ArH), 8.15 (2H, d, 2×ArH).

Preparation of 2-{[2-(3-cyanophenyl)-2-oxoethyl]thio}benzoic acid (VIB 411)

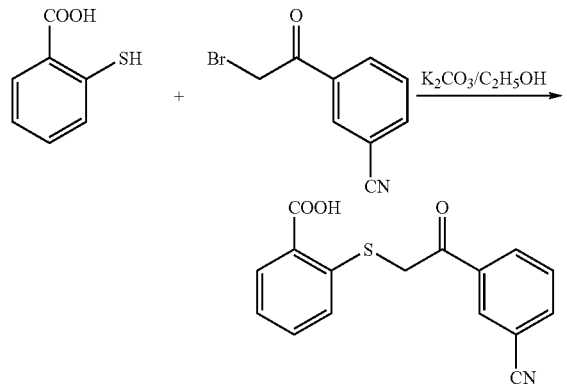

To 3-cyanobromoacetophenone (250 mg, 1.11 mmole) and anhydrous K2CO3 (617 mg, 4.46 mmole) in ethanol (20 ml), 172 mg (1.11 mmole) 2-mercaptobenzoic acid was added and the mixture refluxed overnight. The solvent was evaporated and water added to the solid residue. The basic aqueous solution was extracted with ethyl acetate to remove unreacted bromoacetophenone. The aqueous layer was acidified and extracted with ethyl acetate, washed, dried and evaporated to yield solid (290 mg). m/z 296 (M−1)+$^1$HNMR (DMSO) δ 4.75 (2H, s, —CH2-), 7.22 (1H, t, ArH), 7.49 (2H, t, 2×ArH), 7.74 (1H, t, ArH), 7.88 (1H, d, ArH), 8.12 (1H, d, ArH), 8.3 (1H, d, ArH), 8.54 (1H, s, ArH).

Preparation of 2-{[2-(3-carboxyphenyl)-2-oxoethyl]thio}benzoic add (VIB 412)

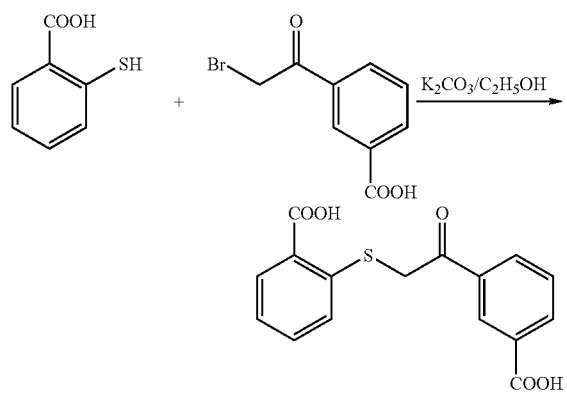

To 3-carboxybromoacetophenone (250 mg, 1.03 mmole) and anhydrous K2CO3 (568.6 mg, 4.11 mmole) in ethanol (20 ml), 158.6 mg (1.03 mmole) 2-mercaptosuccinic acid was added and the mixture refluxed overnight. The solvent was evaporated and water added to the solid residue. The aqueous layer was acidified and extracted with ethyl acetate, washed, dried and evaporated to yield solid (250 mg). m/z 315 (M−1)+1HNMR (DMSO) δ 4.75 (2H, s, —CH2-), 7.22 (2H, t, 2×ArH), 7.48 (2H, t, 2×ArH), 7.67, 1H, t, ArH), 7.87 (1H, d, ArH), 8.2 (1H, d, ArH), 8.3 (1H, d, ArH), 8.53 (1H, s, ArH).

Preparation of 4-[(2E)-3-phenylprop-2-enoyl]benzoic acid (VIB 237)

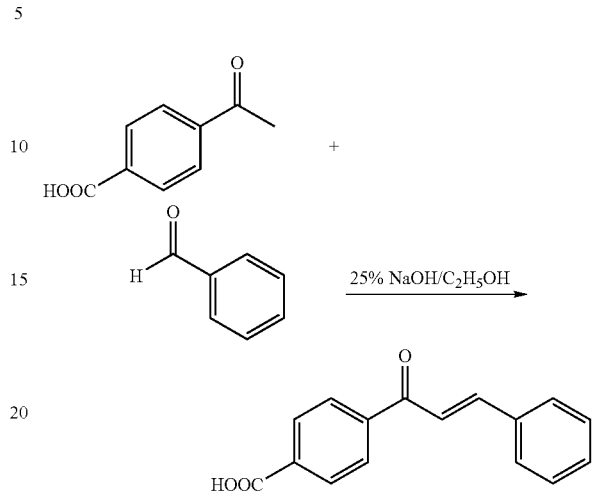

To a mixture of 4-carboxyacetophenone (250 mg, 1.52 mmole) and benzaldehyde (161.6 mg, 1.52 mmole) in absolute ethanol (4 ml), NaOH (25% w/v, 4 ml) was added and allowed to stir at RT for 2 days. Water was added and the mixture acidified to pH 4. The precipitate was filtered, dried and recrystalized with methanol to yield product (98 mg). m/z 251 (M−1)+1HNMR (DMSO) δ 7.4-7.92 (7H, m, ArH & =CH), 8.09 (2H, d, 2×ArH), 8.19 (2H, d, 2×ArH).

[3-(3-Hydroxyphenyl)-2-mercaptobut-2-enoylamino]acetic add (VIB-383)

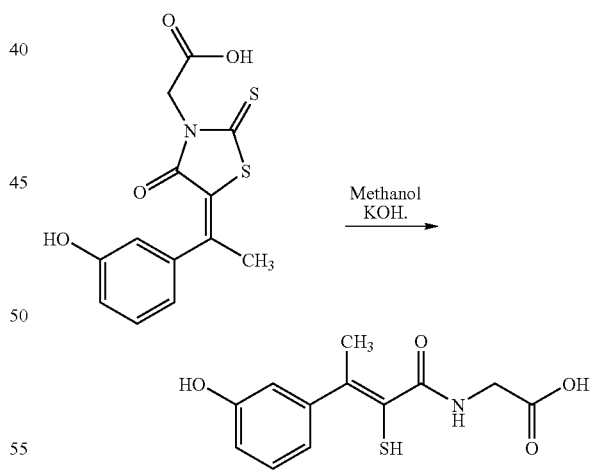

5-(-Methyl-3-hydroxybenzylidine)rhodanine acetic acid (100.0 mg, 0.33 mmol) was added to a solution of potassium hydroxide (90.7 mg, 1.62 mmol) in methanol (10.0 mL). The reaction mixture was stirred at room temperature for 2 hours. The reaction mixture was then poured into saturated sodium chloride (100.0 mL) and the resulting aqueous solution was acidified with glacial acetic acid. A yellow precipitate formed, which was collected by filtration and dried to afford a crude sample of the desired 3-(2-hydroxyphenyl)buten-2-oic acid as a yellow solid which was purified by recrystallisation from propanol to afford (253.6 mg, 100.0%) of the desired 3-(2-hydroxyphenyl)buten-2-oic acid as a yellow powder. M.S. m/z 266 (M−1)+. ¹H NMR (300.13 MHz, CD₃OD) δ 1.12 (3H, s, CH₃), 2.2 (2H, s, CH₂), 5.78 (3H, m, 3×ArH).

5-(-Methyl-3-hydroxybenzylidine)rhodanine-3-acetic acid (VIB-374)

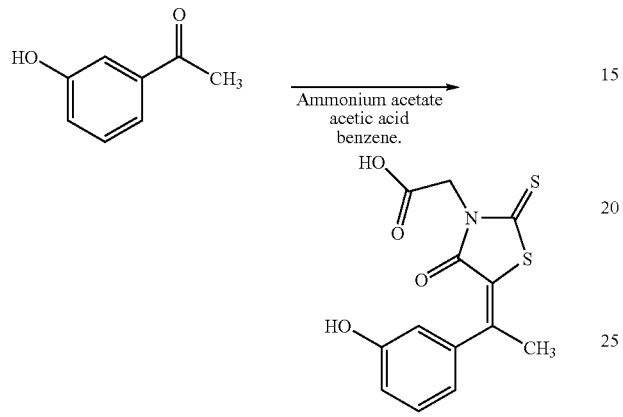

Rhodanine-3-acetic acid (2.81 g, 14.7 mmol) was added to a stirring solution of ammonium acetate (120.0 mg) and glacial acetic acid (360.0 L) in anhydrous benzene (30.0 mL). The reaction mixture was stirred to boiling for 5 minutes. 3-Hydroxyacetophenone (2.0 g, 14.7 mmol) was then added to the reaction mixture and the flask was connected to a Dean Stark trap. The reaction mixture was then heated to reflux overnight, then allowed to cool to room temperature after which the solvent was evaporated under reduced pressure to afford a orange/red gum, which was purified with column chromatography eluting with (chloroform/methanol/acetic acid) (95/5/10 drops) to afford the desired 5-(-methyl-3-hydroxybenzylidine)rhodanine-3-acetic acid as a viscous red oil. M.S. m/z 307 (M−2)+. ¹H NMR (DMSO-d₆) δ 1.9 (3H, s, CH₃), 2.7 (2H, s, CH₂), 6.85 (2H, m, 2×ArH), 7.28 (1H, m, ArH), 8.28 (1H, s, OH).

4-Phenethyloxycinnamic acid (VIB-299)

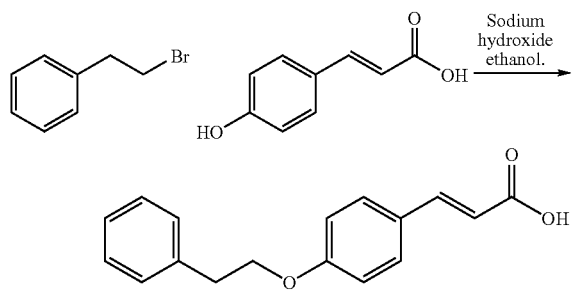

Aqueous 1N Sodium hydroxide solution (6.0 mL, 12.0 mmol) was added to a solution of 4-hydroxycinnamic acid (536.0 mg, 3.2 mmol) in ethanol (10.0 mL). 2-Bromoethylbenzene (575.0 mg, 3.1 mmol) was then added to the reaction mixture and the resulting reaction mixture was stirred at room temperature overnight. The solvent was evaporated under reduced pressure to afford a white residue, which was taken up in water. The aqueous phase was then acidified with concentrated hydrochloric acid to produce a white precipitate which was isolated by filtration and washed with water, then dried to afford (544.0 mg, 66.8%) of the desired 4-phenethyloxycinnamic acid as a white powder. ¹H NMR (300 MHz, DMSO) δ 3.82 (3H, s, OCH₃), 4.78 (2H, s, CH₂), 6.92 (2H, d, 2×ArH, J=7.5 Hz), 7.16 (2H, d, 2×ArH, J=7.5 Hz), 7.52-7.60 (1H, m, ArH), 7.62-7.72 (1H, m, ArH), 7.98 (1H, m, ArH).

Preparation of
3-Benzyloxy-1-benzo[b]thiophene-2-carboxylic acid (VIB 333)

(a) Methyl 3-hydroxy-1-benzo[b]thiophene-2-carboxylate

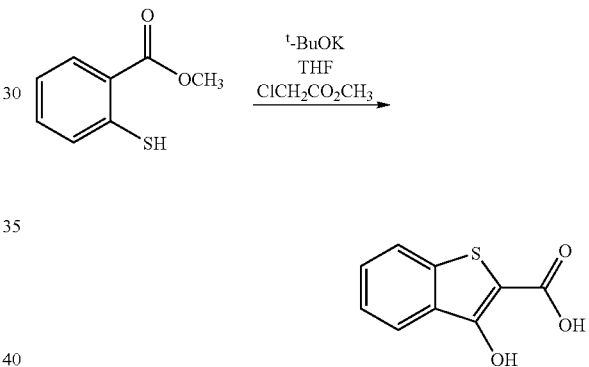

Potassium tertiary butoxide (3.7 g, 32.9 mmol) was added to a solution of methyl thiosalicylate (5.0 g, 29.7 mmol) dissolved in anhydrous THF (40.0 mL). The resultant yellow suspension was stirred at room temperature for 30 minutes at room temperature. Methyl chloroacetate (2.86 mL, 32.6 mmol) was then added dropwise to the reaction mixture and the reaction mixture was stirred at room temperature for 15 minutes and then heated to reflux for 35 minutes. The reaction mixture was then allowed to cool to approximately 40° C. and another batch of potassium tertiary butoxide (3.7 g, 32.9 mmol) was added and the reaction mixture was allowed to heat to reflux for 20 hours. aqueous 2.5N sodium hydroxide (30.0 mL) was added and the reaction mixture was heated to reflux overnight. The reaction mixture was allowed to cool and the methanol was evaporated under reduced pressure to afford a white residue which was taken up in water and the aqueous solution was acidified with concentrated hydrochloric acid and a pink solid precipitated and was collected by filtration. The pink product was purified by recrystallisation from methanol with the addition of charcoal to afford (912.6 mg, 64.0%) of the desired 3-benzyloxy-1-benzo[b]thiophene-2-carboxylic acid as white crystals. M.S. m/z 382 (M+1)+. ¹H NMR (CDCl₃) δ

3.62 (3H, s, OCH3), 5.19 (2H, s, OCH$_2$), 6.49 (1H, m, ArH, 6.7 (1H, m, ArH), 6.78-6.82 (2H, m, 2×ArH), 6.88-7.15 (3H, m, 3×ArH), 7.62 (1H, m, ArH), 10.05 (1H, s, NH).

(b) Methyl 3-benzyloxy-1-benzo[b]thiophene-2-carboxylate

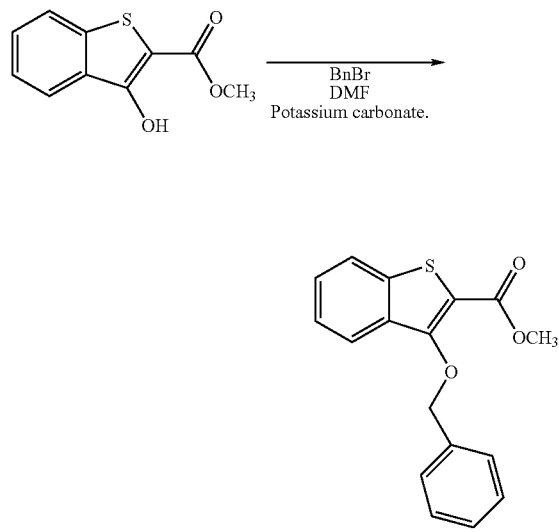

Potassium carbonate (4.1 g, 29.6 mmol) was added as a solid to a solution of 3-hydroxy-1-benzo[b]thiophene-2-carboxylate (1.4 g, 6.7 mmol) and benzyl bromide (1.2 mL, 10.1 mmol) in anhydrous DMF (15.0 mL) at room temperature. The reaction mixture was heated at 60° C. overnight. The reaction mixture was allowed to cool to room temperature, filtered and the DMF was evaporated under reduced pressure to afford a yellow solid which was purified with column chromatography eluting with (ethyl acetate/hexane) (1/19) to afford a white powder which was further purified by recrystallisation from hexane to afford (2.84 g, 66.0%) of the desired methyl-3-benzyloxy-1-benzo[b]thiophene-2-carboxylate as fluffy white needles. M.S. m/z 382 (M+1)$^+$. $^1$H NMR (DMSO-d$_6$) δ 3.8 (2H, s, OCH$_2$), 3.81 (3H, s, OCH$_3$), 7.01-7.04 (2H, m, 2×ArH), 7.05-7.40 (2H, m, 2×ArH), 7.57-7.67 (4H, m, 4×ArH), 8.81 (1H, s, NH).

(c) 3-Benzyloxy-1-benzo[b]thiophene-2-carboxylic acid (VIB 333)

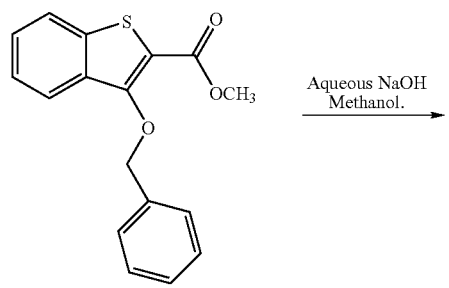

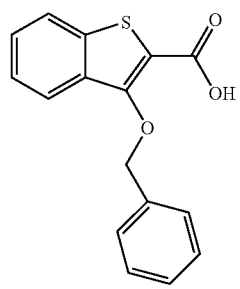

Methyl 3-benzyloxy-1-benzo[b]thiophene-2-carboxylate (1.5 g, 5.0 mmol) was dissolved in methanol (50.0 mL) and aqueous 2.5N sodium hydroxide (30.0 mL) was added and the reaction mixture was heated to reflux overnight. The reaction mixture was allowed to cool and the methanol was evaporated under reduced pressure to afford a white residue which was taken up in water and the aqueous solution was acidified with concentrated hydrochloric acid and a pink solid precipitated and was collected by filtration. The pink product was purified by recrystallisation from methanol with the addition of charcoal to afford (912.6 mg, 64.0%) of the desired 3-benzyloxy-1-benzo[b]thiophene-2-carboxylic acid as white crystals. M.S. m/z 382 (M+1)$^+$. $^1$H NMR (CDCl$_3$) δ 3.62 (3H, s, OCH$_3$), 5.19 (2H, s, OCH$_2$), 6.49 (1H, m, ArH, 6.7 (1H, m, ArH), 6.78-6.82 (2H, m, 2×ArH), 6.88-7.15 (3H, m, 3×ArH), 7.62 (1H, m, ArH), 10.05 (1H, s, NH).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

TABLE 1

Fc Receptor Modulating Compounds According to the Present Invention

| Compound Name | Structure | Concentration at 50% inhibition of platelet activation by HAGG (micM) |
|---|---|---|
| 001 | [structure: fluorenone with two COOH groups] | 600 |
| 026 | [structure: 6-nitro-3-chloro-benzothiophene-2-carboxylic acid] | 100 |
| 032 | [structure: bis(3-carboxyphenyl) sulfoxide] | 70 |
| 044 | [structure: 6-nitro-3-chloro-benzothiophene-2-carboxylic acid S-oxide] | 230, 230 |
| 090 | [structure: 7-methoxy-3-isopropoxy-benzothiophene-2-carboxamide tetrazole] | 195, 295 |
| 092 | [structure: 5-methoxy-4-nitro-3-(1-methylethoxy)-benzothiophene-2-carboxamide tetrazole] | 630, 435 |
| 216 | [structure: 1-(3-cyanophenyl)-2-((3-carboxyphenyl)thio)ethanone] | 240, 240 |

TABLE 1-continued

Fc Receptor Modulating Compounds According to the Present Invention

| Compound Name | Structure | Concentration at 50% inhibition of platelet activation by HAGG (micM) |
|---|---|---|
| 217 | [structure: 1,3-disubstituted benzene with COOH, connected via C(=O)CH2-S- to 3-carboxyphenyl] | 360, >630 |
| 238 | [structure: 2-carboxyphenyl-CH=CH-C(=O)-pyrrole] | 270 |
| 239 | [structure: 3-(HOOC)phenyl-S-CH2CH2CH2-CN] | 330 |
| 261 | [structure: 2,4,5-trinitro-7-carboxy-fluoren-9-one] | <140 (IC67) |
| 276 | [structure: 5-methoxy-3-(cyclohexyloxy)-benzo[b]thiophene-2-carboxylic acid] | <165 (IC79), 170 |
| 292 | [structure: bis(3-carboxyphenacyl) sulfide] | 520 |
| 294 | [structure: phenacyl 3-carboxyphenyl sulfide] | <190 (IC89), 135, 155 |

TABLE 1-continued

Fc Receptor Modulating Compounds According to the Present Invention

| Compound Name | Structure | Concentration at 50% inhibition of platelet activation by HAGG (micM) |
|---|---|---|
| 297 | (3-hydroxyphenyl)-CH=C(SH)-COOH | 190 |
| 299 | PhCH₂CH₂O-(4-phenyl)-CH=CH-COOH | 410 |
| 237 | 4-(HO₂C)C₆H₄-CO-CH=CH-Ph | 40 |
| 410 | 4-(HO₂C)C₆H₄-CO-CH₂-S-(2-CO₂H-C₆H₄) | 50 |
| 411 | 3-(CN)C₆H₄-CO-CH₂-S-(2-CO₂H-C₆H₄) | 180 |
| 412 | 3-(CO₂H)C₆H₄-CO-CH₂-S-(2-CO₂H-C₆H₄) | 60 |
| 294 | 3-(CO₂H)C₆H₄-S-CH₂-CO-Ph | 80 |

TABLE 1-continued
Fc Receptor Modulating Compounds According to the Present Invention
| Compound Name | Structure | Concentration at 50% inhibition of platelet activation by HAGG (micM) |
|---|---|---|
| 350 | 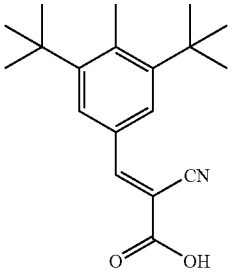 | 290 |
| 383 | 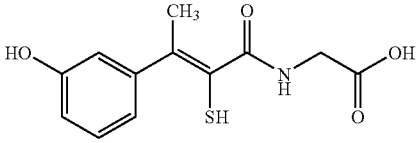 | 280 |
| 333 | 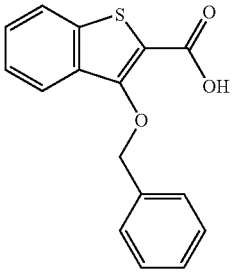 | 520 |
| 384 | 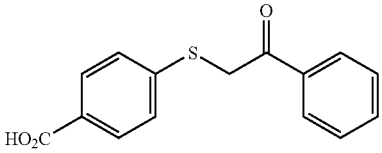 | 170 |
| 385 | 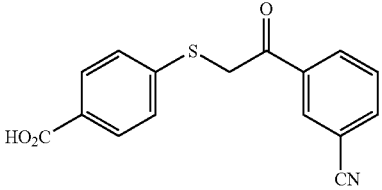 | 360 |

| Compound No | Structure | % Inhibition of platelet Activation |
|---|---|---|
| 027 | 3-HOOC-C6H4-CH(O)CH-C(O)-C6H4-3-COOH (trans-epoxide) | 0, 84, 49 |
| 076 | 3-HOOC-C6H4-N=CH-C6H4-3-COOH | 13 |
| 080 | 3,5-Cl2-C6H3-NH-N=CH-C6H4-3-COOH | Insoluble |
| 081 | 3-HOOC-C6H4-N=CH-C6H4-4-COOH | 83 |
| 100 | 3-HOOC-C6H4-NH-CH2-C6H4-3-COOH | 7 |
| 114 | 3,5-(HOOC)2-C6H3-N=CH-C6H4-3-COOH | 8 |
| 192 | 3-HOOC-C6H4-NH-C(O)-NH-C6H4-3-COOH | 22, 19 |
| 197 | C6H5-CH2-O-C(O)-NH-(CH2)5-COOH | 91, 26, 87, 93 |

-continued
| Compound No | Structure | % Inhibition of platelet Activation |
|---|---|---|
| 200 | 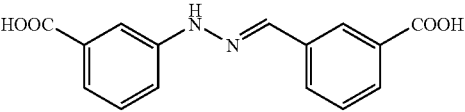 | 98, 54, 95 |
| 219 | 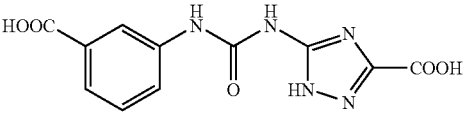 | Not yet tested |
| 233 | 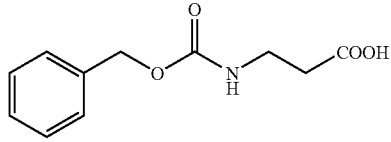 | 74, 67, 87, 24, 74 |
| 234 | 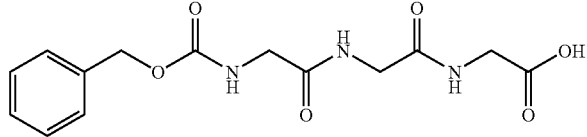 | 25, 54, 27 |
| 235 | 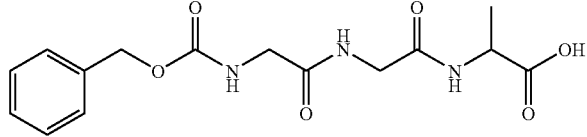 | 30, 49, 54 |
| 236 | 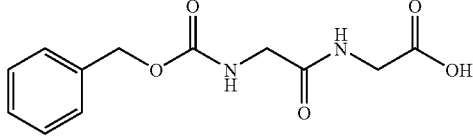 | 34, 33, 65 |
| 255 | 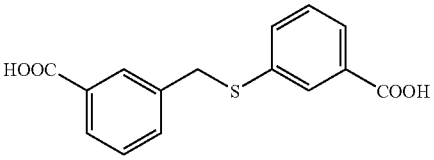 | 11, 25, 21, 39 |
| 331 | 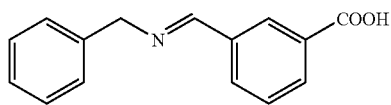 | 17, 58, 37 |
| 336 | 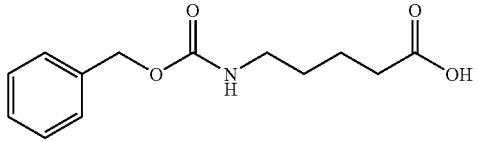 | 15, 65, 53 |
| 337 | 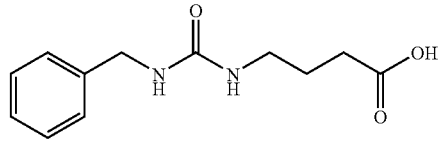 | 4, 5, −45 |

-continued

| Compound No | Structure | % Inhibition of platelet Activation |
|---|---|---|
| 338 | Ph-CH2-NH-C(=O)-NH-(CH2)3-COOH | 10, 43, 27 |
| 339 | Ph-CH2-NH-C(=O)-NH-(CH2)4-COOH | 0, 46, 35 |
| 340 | 3-(H3COOC)-C6H4-NH-C(=O)-NH-(CH2)2-COOH | 2, 54, 46 |
| 341 | 3-(H3COOC)-C6H4-NH-C(=O)-NH-(CH2)3-COOH | 9, 66, 62 |
| 343 | Ph-CH2-NH-C(=O)-CH2-COOH | 0, 39, 25 |
| 344 | Ph-CH2-NH-C(=O)-(CH2)2-COOH | 2, 42, 28 |
| 355 | Ph-CH2-O-C(=O)-NH-(CH2)2-COOH | 6, 43, 9 |
| 342 | 3-(H3COOC)-C6H4-NH-C(=O)-NH-(CH2)4-COOH | 26, 80, 76 |

TABLE 2

Summary of most active small molecule inhibitors

| Compound | IN VITRO TESTING | | IN VIVO TESTING | |
|---|---|---|---|---|
| | IC50 | | Dose Schedule 1 | Dose |
| | ELISA (mM) | Platelet Inhibition (mM) | (7.5 mg/day on days 21, 24, 27, 30) | Schedule 2 (0.33 mg/day 21-34) |
| VIB001 | 12.2 | 0.61 | | |
| VIB032 | 2.8 | -'ve | | yes |
| VIB153 | 8.4 | 0.56 | yes | yes |
| VIB238 | 17.5 | 0.27 | | yes |
| VIB237 | 6.2 | 0.04 | | |
| VIB113 | 8.4 | 1.20 | yes | yes |
| VIB152 | 1.8 | 0.31 | yes | |
| VIB197 | 9.4 | 1.30 | yes | yes |
| VIB216 | 3.0 | 0.25 | | |
| VIB217 | 6.1 | 0.32 | | |
| VIB294 | 6.0 | 0.08 | | yes |
| VIB384 | 4.8 | 0.17 | yes | |
| VIB385 | 6.8 | 0.36 | yes | |
| VIB410 | 6.9 | 0.05 | | |
| VIB411 | 7.8 | 0.18 | | |
| VIB412 | 7.0 | 0.06 | | |
| VIB239 | -'ve | 0.33 | | |
| VIB292 | 5.6 | 0.52 | | |
| VIB297 | 5.6 | 0.19 | | yes |
| VIB299 | 7.2 | 0.41 | | yes |
| VIB350 | 1.3 | 0.29 | | |
| VIB383 | 1.0 | 0.28 | | |
| VIB333 | 1.6 | 0.52 | | |
| VIB026 | 17.5 | 0.78 | | |
| VIB374 | 2.0 | 0.22 | | |

The invention claimed is:

1. A method for treating an autoimmune disease involving Fc receptor activity comprising administering to a subject in need of treatment one or more compounds having the general formula II:

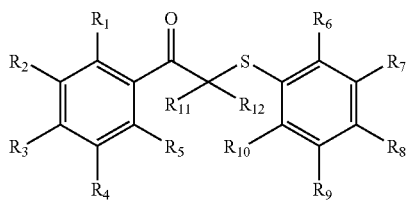

II wherein

R1, R2, R3, R4, R5, R6, R7, R8, R9, and R10 are each independently selected from H, halogen, $NO_2$, CN, $C_{1-6}$ alkyl, $CF_3$, aryl, heteroaryl, cylcoalkyl, cycloheteroalkyl, $OCF_3$, OR18, SR18, $OC_{1-6}$ alkyl, $OC_{2-6}$alkylNR18R19, Oaryl, Oheteroaryl, Ocycloalkyl, Ocycloheteroalkyl, $OC_{1-6}$ alkylaryl, $OC_{1-6}$ alkylheteroaryl, $OC_{1-6}$ alkylcycloalkyl, $OC_{1-6}$ cycloheteroalkyl, $CO_2R18$, $C_{1-6}$ alkyl$CO_2R18$, CONR18R19, $C_{1-6}$ alkylCONR18R19, NR18R19, $C_{1-6}$ alkylNR18R19, $NR20C_{1-6}$ alkylNR18R19, $C_{1-6}$ alkyl$NR20C_{1-6}$ alkylNR18R19, NR18COR19, $C_{1-6}$ alkylNR18COR19, $C_{1-6}$ alkylNR20CONR18R19, NR20CONR18R19, $C_{1-6}$ alkyl$NR18SO_2R19$, $NR18SO_2R19$;

R18, R19 are each independently selected from H, $C_{1-4}$ alkyl, $C_{1-4}$ alkyl cycloheteroalkyl, aryl, heteroaryl, $C_{1-4}$ alkyl aryl, $C_{1-4}$ alkyl heteroaryl, or may be joined to form an optionally substituted 3-8 membered ring optionally containing an atom selected from O, S, NR21;

R20, R21 are each independently selected from H, $C_{1-4}$alkyl;

R11, R12 are each independently selected from H, $C_{1-4}$ alkyl, halogen, $OC_{1-4}$ alkyl;

and wherein the autoimmune disease is selected from the group consisting of rheumatoid arthritis, immune thrombocytopenia purpura, systemic lupus erythematosus and Crohn's disease.

2. A method for treating an autoimmune disease involving Fc receptor activity comprising administering to a subject in need of treatment one or more compounds having the general formula II:

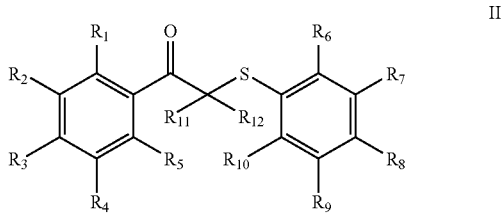

II wherein

R1, R2, R3, R4, R5, R6, R7, R8, R10 are each independently selected from H, $C_{1-4}$ alkyl, $OC_{1-4}$ alkyl, $CO_2H$, CN;

R11, R12 are each independently selected from H, $C_{1-4}$ alkyl;

R9 is independently selected from H, halogen, $NO_2$, CN, $C_{1-6}$ alkyl, $CF_3$, aryl, heteroaryl, cylcoalkyl, cycloheteroalkyl, $OCF_3$, OR18, SR18, $OC_{1-6}$ alkyl, $OC_{2-6}$alkylNR18R19, Oaryl, Oheteroaryl, Ocycloalkyl, Ocycloheteroalkyl, $OC_{1-6}$ alkylaryl, $OC_{1-6}$ alkylheteroaryl, $OC_{1-6}$ alkylcycloalklyl, $OC_{1-6}$ cycloheteroalkyl, $CO_2R18$, $C_{1-6}$ alkyl$CO_2R18$, CONR18R19, $C_{1-6}$ alkylCONR18R19, NR18R19, $C_{1-6}$ alkylNR18R19, $NR20C_{1-6}$ alkylNR18R19, $C_{1-6}$ alkyl$NR20C_{1-6}$ alkylNR18R19, NR18COR19, $C_{1-6}$ alkylNR18COR19, $C_{1-6}$ alkylNR20CONR18R19, NR20CONR18R19, $C_{1-6}$ alkyl$NR18SO_2R19$, $NR18SO_2R19$;

R18, R19 are each independently selected from H, $C_{1-4}$ alkyl, $C_{1-4}$ alkyl cycloheteroalkyl, aryl, heteroaryl, $C_{1-4}$alkyl aryl, $C_{1-4}$ alkyl heteroaryl, or may be joined to form an optionally substituted 3-8 membered ring optionally containing an atom selected from O, S, NR21;

R20, R21 are each independently selected from H, $C_{1-4}$alkyl;

wherein the autoimmune disease is selected from the group consisting of rheumatoid arthritis, immune thrombocytopenia purpura, systemic lupus erythematosus and Crohn's disease.

3. A method for treating an autoimmune disease involving Fc receptor activity comprising administering to a subject in need of treatment one or more compositions comprising:

(a) one or more compounds having the general formula II:

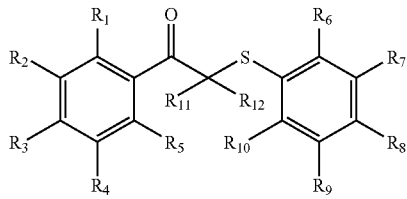

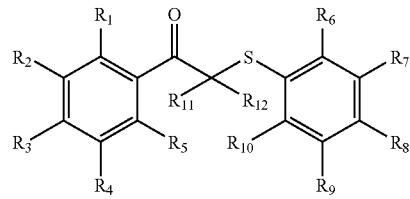

wherein
R1, R2, R3, R4, R5, R6, R7, R8, R9, and R10 are each independently selected from H, halogen, $NO_2$, CN, $C_{1-6}$ alkyl, $CF_3$, aryl, heteroaryl, cylcoalkyl, cycloheteroalkyl, $OCF_3$, OR18, SR18, $OC_{2-6}$alkyl, $OC_{2-6}$ alkylNR18R19, Oaryl, Oheteroaryl, Ocycloalkyl, Ocycloheteroalkyl, $OC_{1-6}$ alkylaryl, $OC_{1-6}$ alkylheteroaryl, $OC_{1-6}$ alkylcycloalkyl, $OC_{1-6}$ cycloheteroalkyl, $CO_2R18$, $C_{1-6}$ alkyl$CO_2R18$, CONR18R19, $C_{1-6}$ alkylCONR18R19, NR18R19, $C_{1-6}$ alkylNR18R19, $NR20C_{1-6}$ alkylNR18R19, $C_{1-6}$ alkyl$NR20C_{1-6}$ alkylNR18R19, NR18COR19, $C_{1-6}$ alkylNR18R19, $C_{1-6}$ alkylNR20CONR18R19, NR20CONR18R19, $C_{1-6}$ alkylNR18$SO_2$R19, NR18$SO_2$R19;

R18, R19 are each independently selected from H, $C_{1-4}$ alkyl, $C_{1-4}$ alkyl cycloheteroalkyl, aryl, heteroaryl, $C_{1-4}$ alkyl aryl, $C_{1-4}$ alkyl heteroaryl, or may be joined to form an optionally substituted 3-8 membered ring optionally containing an atom selected from O, S, NR21;

R20, R21 are each independently selected from H, $C_{1-4}$alkyl;

R11, R12 are each independently selected from H, $C_{1-4}$ alkyl, halogen, $OC_{1-4}$ alkyl;

(b) a pharmaceutically acceptable diluent,
wherein the autoiminune disease is selected from the group consisting of rheumatoid arthritis, immune thrombocytopenia purpura, systemic lupus erythematosus and Crohn's disease.

4. A method for treating an autoimmune disease involving Fc receptor activity comprising administering to a subject in need of treatment one or more compositions comprising:

(a) one or more compounds having the general formula II:

wherein
R1, R2, R3, R4, R5, R6, R7, R8, R10 are each independently selected from H, $C_{1-4}$ alkyl, $OC_{1-4}$alkyl, $CO_2H$, CN;

R11, R12 are each independently selected from H, $C_{1-4}$ alkyl;

R9 is independently selected from H, halogen, $NO_2$, CN, $C_{1-6}$ alkyl, $CF_3$, aryl, heteroaryl, cylcoalkyl, cycloheteroalkyl, $OCF_3$, OR18, SR18, $OC_{1-6}$ alkyl, $OC_{2-6}$ alkylNR18R19, Oaryl, Oheteroaryl, Ocycloalkyl, Ocycloheteroalkyl, $OC_{1-6}$ alkylaryl, $OC_{1-6}$ alkylheteroaryl, $OC_{1-6}$ alkylcycloalklyl, $OC_{1-6}$ cycloheteroalkyl, $CO_2R18$, $C_{1-6}$ alkyl$CO_2R18$, CONR18R19, $C_{1-6}$ alkylCONR18R19, NR18R19, $C_{1-6}$ alkylNR18R19, $NR20C_{1-6}$ alkylNR18R19, $C_{1-6}$ alkyl$NR20C_{1-6}$ alkylNR18R19, NR18COR19, $C_{1-6}$ alkylNR18COR19, $C_{1-6}$ alkylNR20CONR18R19, NR20CONR18R19, $C_{1-6}$ alkylNR18$SO_2$R19, NR18$SO_2$R19;

R18, R19 are each independently selected from H, $C_{1-4}$ alkyl, $C_{1-4}$ alkyl cycloheteroalkyl, aryl, heteroaryl, $C_{1-4}$ alkyl aryl, $C_{1-4}$ alkyl heteroaryl, or may be joined to form an optionally substituted 3-8 membered ring optionally containing an atom selected from O, S, NR21;

R20, R21 are each independently selected from H, $C_{1-4}$alkyl;

(b) a pharmaceutically acceptable diluent,
wherein the autoimmune disease is selected from the group consisting of rheumatoid arthritis, immune thrombocytopenia purpura, systemic lupus erythematosus and Crohn's disease.

* * * * *